US011286496B1

(12) United States Patent
Liu et al.

(10) Patent No.: US 11,286,496 B1
(45) Date of Patent: Mar. 29, 2022

(54) MODIFIED GENES TO INCREASE SEED PROTEIN CONTENT

(71) Applicant: PIONEER HI-BRED INTERNATIONAL, INC., Johnston, IA (US)

(72) Inventors: Zhan-Bin Liu, Clive, IA (US); Bo Shen, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/668,443

(22) Filed: Oct. 30, 2019

Related U.S. Application Data

(60) Provisional application No. 62/753,637, filed on Oct. 31, 2018.

(51) Int. Cl.
*C12N 15/82* (2006.01)

(52) U.S. Cl.
CPC ..... *C12N 15/8251* (2013.01); *C12N 15/8234* (2013.01); *C12N 15/8247* (2013.01)

(58) Field of Classification Search
None
See application file for complete search history.

(56) References Cited

U.S. PATENT DOCUMENTS

2011/0004955 A1\* 1/2011 Abad ............... G01N 33/68
800/275

OTHER PUBLICATIONS

Piper and Boote. "Temperature and Cultivar Effects on Soybean Seed Oil and Protein Concentrations". JAOCS. (76)10: 1233-1241. (Year: 1999).\*
Gomez et al. "Delayed embryo development in the *Arabidopsis* Trehalose-6-Phosphate Synthase 1 mutant is associated with altered cell wall structure, decreased cell division and starch accumulation". The Plant Journal. 46: 69-84. (Year: 2006).\*
Bolon, et al. "Phenotypic and Genomic Analyses of a Fast Neutron Mutant Population Resource in Soybean". Plant Physiology. (156) 240-253. (Year: 2011).\*

\* cited by examiner

*Primary Examiner* — Matthew R Keogh
*Assistant Examiner* — David R Byrnes

(57) ABSTRACT

Soybean seeds with increased protein, oil or protein plus oil and having a modified expression of a reticulon-like polypeptide, modified expression of a trehalose-6-phosphate synthase polypeptide, or modified expression of both sequences are provided. Methods for modifying expression of reticulon-like polypeptides and polynucleotides and trehalose-6-phosphate synthase polypeptides and polynucleotides include genome editing to modify the transcription regulatory region or sequence encoding the reticulon-like and trehalose-6-phosphate synthase polypeptides and transformation with recombinant DNA constructs to enhance or suppress expression.

15 Claims, 2 Drawing Sheets

Specification includes a Sequence Listing.

US 11,286,496 B1

MODIFIED GENES TO INCREASE SEED PROTEIN CONTENT

CROSS-REFERENCE TO RELATED APPLICATIONS

This application claims the benefit of priority to U.S. provisional patent application No. 62/753,637, filed Oct. 31, 2018, the entire disclosure of which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "7837USNP_SeqList_ST25" created on Oct. 29, 2019, and having a size of 109 kilobytes and is filed concurrently with the specification. The sequence listing contained in this ASCII formatted document is part of the specification and is herein incorporated by reference in its entirety.

BACKGROUND

Soybeans are a major agriculture commodity in many parts of the world, and are a source of useful products, such as protein and oil, for human and animal consumption. A valuable product obtained from processed soybeans is soybean meal, which contains a high proportion of protein and is primarily used as a component in animal feed. Soy meal can be further processed to produce soy protein isolates, soy flour or soy concentrates, which can be used in foods, glues and as emulsifiers and texturizers. Soybean plants which produce seeds higher in protein content or protein and oil content may contribute to a higher-value crop.

SUMMARY

Provided are soybean plant, seeds, plant parts and plant cells that have a genomic modification that decreases expression of a reticulon-like and/or a trehalose-6-phosphate synthase polypeptide. The genomic modification can be a deletion, insertion or substitution of nucleotides in a genomic sequence encoding a reticulon-like polypeptide comprising an amino acid sequence that is at least 95% identical to SEQ ID NO: 2 or 4 or a combination thereof, which modification suppresses activity of the reticulon-like polypeptide, such that the plant produces seeds having an oil content of at least 15% by weight and an increased protein content relative to control seeds not comprising the modification.

In some embodiments, the plant comprises on chromosome 10 a polynucleotide encoding a wall-associated receptor kinase comprising an amino acid sequence that is at least 95% identical to SEQ ID NO: 10.

In some embodiments, the modification in the plant comprises a deletion or insertion in a coding sequence of the polypeptide, which may result in a frame-shift of the sequence encoding the polypeptide. In some embodiments, the modification comprises a deletion, insertion or substitution in a transcription regulatory region of the genomic sequence.

Plants producing seeds and seeds are provided, which have an increased PROIL content of at least 5% relative to control seeds not comprising the modification. In some embodiments, the PROIL content of the seeds is at least 55% by weight.

In some embodiments, plants are provided which further include a heterologous nucleic acid sequence such as one or more of a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants.

In some embodiments, methods of plant breeding include crossing the plants provided with a second soybean plant to produce progeny seed. Progeny seed produced by these methods may comprise the modification and have increased protein or PROIL content relative to a control seed not comprising the modification.

Methods are provided for increasing protein content in the seed of a soybean plant, by introducing a modification into a reticulon-like gene and/or a trehalose-6-phosphate synthase gene, or both genes in a soybean plant. Examples of modifications include a deletion, insertion or substitution of nucleotides in a genomic sequence encoding a reticulon-like and/or a trehalose-6-phosphate synthase polypeptide comprising an amino acid sequence that is at least 95% identical to SEQ ID NO: 2 or 4 to produce a modified plant. The modified plant can be grown to produce a modified seed, which has an increased protein or PROIL content compared to a control seed of a control plant not comprising the modification.

In some embodiments, the modification comprises a deletion or insertion in a coding sequence of the polypeptide, which may result in a frame-shift of the sequence encoding the polypeptide. The deletion or insertion may be introduced through targeted DNA breaks. In some embodiments, the modification comprises a deletion, insertion or substitution in a transcription regulatory region of the genomic sequence. The modification may result in enhancement of activity of a repressor binding element, or disruption of a promotor enhancing element.

In some embodiments, the method produces modified seeds having an oil content of at least 15% by weight. In some embodiments, the modified plant comprises on chromosome 10 a polynucleotide encoding a wall-associated receptor kinase comprising an amino acid sequence that is at least 95% identical to SEQ ID NO: 10.

Provided are methods for producing a soybean plant producing a seed comprising increased protein content, by introducing into a soybean plant a recombinant DNA construct comprising a heterologous polynucleotide, the polynucleotide comprising a sequence that results in reduced expression of a polypeptide having at least 95% identity to SEQ ID NO: 2 and/or 4, or a combination thereof and regenerating a plant producing a seed comprising increased protein content. In some embodiments, the reduced expression of the polypeptide is achieved through gene silencing or RNAi. Plants producing seeds and seeds produced by this method are provided, in which the plant or seed comprises the heterologous polynucleotide stably incorporated into its genome, and the seed has an increased protein content compared to control seeds not comprising the heterologous polynucleotide. In some embodiments, the seed or progeny seed produced by the plant has an oil content of at least 15%, an increased protein or PROIL content compared to a control seed not comprising the heterologous polynucleotide.

Provided are soybean plants, seeds, plant parts and plant cells comprising a modification comprising a deletion of genomic sequence corresponding to the sequence beginning at position 2268 of SEQ ID NO: 11 and ending at position 22,384 of SEQ ID NO 11 which can have an oil content of at least 15% by weight and an increased protein content relative to a control seed not comprising the modification.

Provided are guide RNA sequences, and recombinant DNA constructs expressing the guide RNAs, that target a genomic locus of a plant cell, which contains a polynucleotide encodes a polypeptide comprising an amino acid sequence that is at least 90% identical to SEQ ID NO: 2 or 4, or both 2 and 4. Soybean plant cells, plants and seeds comprising the guide RNA sequence are provided seeds, such as produced by the plant or regenerated from the plant cell have an oil content of at least 15% and an increased protein content compared to control seeds not comprising the guide RNA sequence.

Provided are methods of detecting the presence of a polynucleotide comprising a sequence disclosed herein, such as SEQ ID NO: 19, by contacting a DNA sample obtained from a soybean plant which comprises SEQ ID NO: 19 with a first primer molecule which binds to a genomic region upstream of SEQ ID NO: 19 or at least partially contained in SEQ ID NO: 19 and a second primer molecule which binds to a genomic region downstream of SEQ ID NO: 19 or at least partially contained in SEQ ID NO: 19. A nucleic acid amplification reaction condition is provided and performed to produce a DNA amplicon molecule, such as 48 to 5000 nucleotides in length, which indicates the presence of SEQ ID NO: 19 and which is detected. In some embodiments, the first or second primer molecule binds to a sequence corresponding to (a) position 1 to position 2268 of SEQ ID NO: 11, or a complement thereof, or (b) position 22,384 to position 24,650 of SEQ ID NO: 11, or a complement thereof, or the first and second primer molecules bind to a sequence corresponding to (a) position 1 to position 2268 of SEQ ID NO: 11, or a complement thereof, and (b) position 22,384 to position 24,650 of SEQ ID NO: 11, or a complement thereof, respectively.

BRIEF DESCRIPTION OF THE SEQUENCES

TABLE 1

Figure 1:
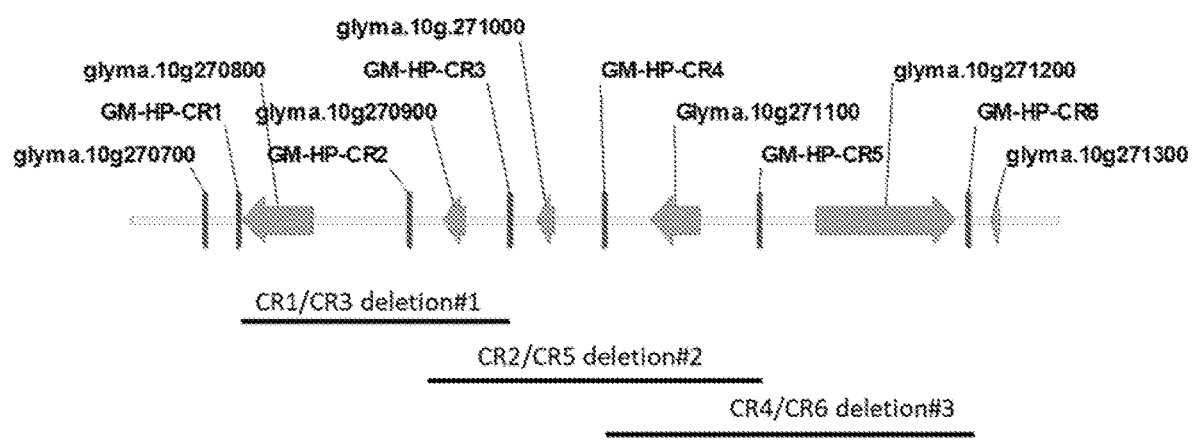
FIG. 1 is a schematic drawing showing the genomic map of the high-protein region on chromosome 10 and fine mapping using three deletion lines.

Listing of sequences used in this application

| Sequence Description | SEQ ID NO: |
|---|---|
| Polynucleotide encoding the glyma.10g270900 reticulon-like polypeptide | 1 |

TABLE 1-continued

Listing of sequences used in this application

| Sequence Description | SEQ ID NO: |
|---|---|
| Glyma.10g270900 reticulon-like polypeptide | 2 |
| Polynucleotide encoding the glyma.10g270800 trehalose-6-phosphate synthase polypeptide | 3 |
| Glyma.10g270800 trehalose-6-phosphate synthase polypeptide | 4 |
| Polynucleotide encoding the glyma.10g271000 polypeptide Glyma.10g271000 polypeptide | 5 |
| polypeptide Glyma.10g271000 polypeptide | 6 |
| Polynucleotide encoding the glyma.10g271100 polypeptide Glyma.10g271100 polypeptide | 7 |
| polypeptide Glyma.10g271100 polypeptide | 8 |
| Polynucleotide encoding the glyma.10g271200 polypeptide Glyma.10g271200 polypeptide | 9 |
| polypeptide Glyma.10g271200 polypeptide | 10 |
| Genomic wild-type soybean polynucleotide region targeted by deletions | 11 |
| GM-HP-CR1 | 12 |
| GM-HP-CR3 | 13 |
| GM-HP-CR2 | 14 |
| GM-HP-CR5 | 15 |
| GM-HP-CR4 | 16 |
| GM-HP-CR6 | 17 |
| GM-RET-CR1 | 18 |
| Border junction sequence of the 20K base pair (bp) deletion occurring in CR1/CR3 deletion line #1 | 19 |

DETAILED DESCRIPTION

Compositions and methods related to modified plants producing seeds high in protein are provided. Plants that have been modified using genomic editing techniques, transformation or mutagenesis to produce seeds having increased protein are provided. Suitable plants include oil-seed plants, such as palm, canola, sunflower and soybean as well as, without limitation, rice, cotton, sorghum, wheat, maize, alfalfa and barley. Modifying expression of a reticulon-like polypeptide in a plant such as soybean or modifying the coding sequence of the reticulon-like polypeptide, results in a seed with high-seed protein relative to a comparable seed not comprising the modification. The modification can be introduced using genomic editing technology, transformation or mutagenesis, such as described herein. Plants, such as soybean plants, that show reduced expression of a reticulon-like polypeptide, a trehalose-6-phosphate synthase, or a combination thereof, and which are robust, high-yielding and produce seeds containing increased protein are provided. In some embodiments, the modified plant with reduced reticulon-like polypeptide expression further comprises a modification to sequence relating to oil accumulation, resulting in seeds having increased oil content relative to seeds of a control plant not comprising the modification.

Unless specified otherwise, protein, oil, PROIL, fiber, stachyose, sucrosyl-oligosaccharide and other components are measured by weight at or adjusted to a 13% moisture basis in the soybean seed. Seeds, plants (or plant parts thereof) producing seeds, and methods of making or using the seeds and plants (or plant parts thereof) and having the seed compositions described herein are provided.

Provided are modified soybean seeds and plants producing such seeds, as described herein, containing a substantially similar or increased oil content compared with a comparable unmodified, control, null or wild-type seed. The oil content of the modified seed may be at least or at least about 15%, 16%, 17%, 18%, 19%, 19.5%, 20%, 20.5%, 21%, 21.5%, 22%, 22.5%, 23%, 23.5%, 24%, 24.5%, or 25% oil and less than or less than about 32%, 31%, 30%, 29%, 28%, 27%, 26%, 25%, 24.5%, 24%, 23.5%, 23%, 22.5%, 22%, 21.5%, 21%, 20.5% or 20% oil. The modified soybean seed may contain an oil content that is at least 70%, 75%, 80%, 85%, 90%, 95%, 100%, 105%, 110%, 115% or 120% and less than 150%, 140%, 130%, 120% or 110% or the amount of oil in a comparable unmodified, control, null or wild-type seed.

Provided are modified soybean seeds and plants producing such seeds, as described herein, containing an increased amount of protein plus oil relative to a control, comparable unmodified or null seed or plant producing such seed. For the sum of oil and protein content, also referred to as the PROIL content, the modified soybean seed such as described herein may contain at least or at least about 54%, 55%, 56%, 57%, 58%, 59%, 60%, 61%, 62% or 63% PROIL and less than or less than about 70%, 65%, 60%, 59%, 58%, 57%, 56%, or 55% PROIL by weight compared with the comparable unmodified or null soybean containing at least or at least about 45%, 46%, 47%, 48%, 49%, 50%, 51%, 52% or 53% PROIL and less than or less than about 56%, 55%, 54%, 53%, 52%, 51%, 50%, or 49% PROIL. Useful examples of percent point increases in PROIL in a seed, such as a modified soybean seed described herein, compared with a comparable null unmodified or control soybean include, but are not limited to, percentage point increases by weight of at least or at least about 1, 2, 3, 4, or 5% and less than or less than about 15, 14, 13, 12, 11, 10, 9, 8, 7, or 6%.

Provided are seeds and plants producing seed comprising a modification and having an amount of stachyose of about or at least about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0% and less than about 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1% or 2.0% stachyose (percentage points by weight).

Provided are seeds and plants producing seed comprising a modification and having an amount of sucrosyl-oligosaccharide of about or at least about 0.5%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9% or 3.0% and less than about 5.5%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, or 2.5% sucrosyl-oligosaccharide (percentage points by weight).

Provided are soybean seeds comprising a modification having a fiber content decrease in the seed of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 percentage points by weight and less than 8.0, 7.9, 7.8, 7.7, 7.6, 7.5, 7.4, 7.3, 7.2, 7.1, 7.0, 6.9, 1.8, 6.7, 6.6, 6.5, 6.4, 6.3, 6.2, 6.1, 6.0, 5.9, 5.8, 5.7, 5.6, 5.5, 5.4, 5.3, 5.2, 5.1 or 5.0 percentage points by weight compared with a control plant not comprising the modification. Provided are soybean seeds having a fiber content in the seeds of less than 8.0, 7.5, 7.0, 6.5, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1 or 3.0% (percentage points by weight) and at least 1.0, 1.5, 2.0, 2.5 or 3.0% (percentage points by weight).

The soybean seeds can be efficiently processed to produce meal (either high-protein meal produced from dehulled beans or conventional meal produced from whole soybeans) having a high protein content compared with comparable meal produced from comparable seeds that do not contain the modification. In some embodiments, meal is provided which has a protein content that is increased by at least 0.5, 1.0, 1.5, 2.0, 2.5, 3.0, 3.5, 4.0, 4.5 or 5.0% percent by weight and less than 12.0, 11.0, 10.0, 9.0, 8.0, 7.0, 6.0 or 5.0% by weight compared to meal prepared from a control soybean seed not comprising the modification, such as a null, unmodified or wild-type soybean seed. The meal may be prepared from a plant comprising the modification and may comprise a modified polynucleotide described herein.

Provided are modified soybean seeds and plants, plant parts and plant cells which have an increased protein or PROIL content and at least a comparable or increased yield, such as described herein, relative to a comparable control unmodified seed and plant, plant part or plant cell not comprising the modification.

The modified polypeptides and polynucleotides described herein include or encode reticulon-like polypeptides or trehalose-6-phosphate synthase polypeptides, or a combination thereof. Reticulon-like polypeptides are a group of proteins found in the endoplasmic reticulum and have diverse functions, including a role in promoting membrane curvature, vesicle formation, trafficking and regulating oil and protein biosynthesis in the endoplasmic reticulum. The carboxy-terminal reticulon homology domain often found in reticulon-like proteins has two hydrophobic regions, each about 30 amino acids in length, flanking a hydrophilic loop of 60-70 amino acids. Trehalose-6-phosphate synthase is an enzyme catalyzing the first step in trehalose synthesis. It plays a role in regulating stress response, sugar sensing, growth and development, such as flowering and embryo development.

Unless expressly stated to the contrary, "soybean" means a soybean plant or seed of *Glycine max*. Provided are soybean plants, plant cell, plant parts and seeds which have had expression of a polypeptide or polynucleotide sequence that encodes the polypeptide suppressed, knocked out, decreased or inhibited. Examples of polypeptides include the reticulon-like polypeptide shown in SEQ ID NO: 2, encoded by glyma.10g270900 (SEQ ID NO: 1) and the trehalose-6-phosphate polypeptides shown in SEQ ID NO: 4, encoded by the glyma.10g270800 coding sequence (SEQ ID NO: 3). In some embodiments, soybean plants, seeds, plant cells and methods are provided in which expression of both the reticulon-like polypeptide and the trehalose-6-phosphate polypeptide is reduced or suppressed.

In some embodiments, the modification results in the suppression of the native reticulon-like polypeptide shown in SEQ ID NO: 2, encoded by glyma.10g270900 (SEQ ID NO:1), and/or the native trehalose-6-phosphate synthase polypeptide shown in SEQ ID NO: 4, encoded by glyma.10g270800 (SEQ ID NO: 3), or both polypeptides. The genome is modified to knock-out, silence, reduce or suppress expression of the native glyma.10g270900 or glyma.10g270800 polypeptide, or both, such as by disrupting the reading frame through insertion or deletion of one or more single bases or short or long sequences, introducing a sufficient number of SNPs to disrupt function or by modifying a transcription regulatory sequence in the transcription regulatory region to include for example repressor elements, repressor binding elements or disrupted promotor enhancer elements to reduce or prevent expression of the glyma.10g270900 or glyma.10g270800 polypeptide, or both. In some embodiments, the expression level of the polynucleotide or polypeptide in a tissue or organ of interest, such as the seed, seed endosperm, embryo, leaf, root or stalk, is less than 95, 90, 85, 80, 75, 70, 65, 60, 55, 50, 45, 40, 35, 30, 25, 20, 15, 10, 5, 4, 3, 2, or 1% of the expression level of the polynucleotide or polypeptide in a comparable control, unmodified or null tissue or organ of interest. Plants producing seeds with increased protein as described herein are obtained.

In some embodiments, the soybean plant, plant cell, plant part or seed includes or expresses the sequences shown in SEQ ID NOs: 5, 6, 7, 8, 9, 10 or any combination thereof, or sequences sharing a percent identity with such sequences. In some embodiments, the soybean plant, plant cell, plant part or seed includes or expresses glyma.10g271200 (SEQ ID NO: 9), encoding a wall-associated receptor kinase (SEQ ID NO: 10).

In some embodiments, the soybean plant, plant cell, plant part or seed includes a recombinant DNA construct or molecule or suppression construct described herein which suppresses or reduces expression of the polypeptide. Transformation methods for producing such soybean plants, plant cells, plant parts or seeds are provided.

In some embodiments, the soybean plant further includes a heterologous nucleic acid sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants. The heterologous nucleic acid may be introduced by backcrossing or transformation.

Provided are polynucleotides that have at least about or at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference nucleotide sequence, such as a nucleotide sequence disclosed in the sequence listing herein, using one of the alignment programs described herein using standard parameters, as well as nucleotide substitutions, deletions, insertions, fragments thereof, and combinations thereof.

An "isolated polynucleotide" generally refers to a polymer of ribonucleotides (RNA) or deoxyribonucleotides (DNA) that is single- or double-stranded, optionally containing synthetic, non-natural or altered nucleotide bases, that is no longer in its natural environment and have been placed in a difference environment by the hand of man, for example in vitro. An isolated polynucleotide in the form of DNA may be comprised of one or more segments of cDNA, genomic DNA or synthetic DNA.

A "recombinant" nucleic acid molecule (or DNA) is used herein to refer to a nucleic acid sequence (or DNA) that is in a recombinant plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A transcription regulatory element or sequence, or a regulatory element or sequence generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

In some embodiments, the modified polynucleotide includes a modified transcriptional enhancer sequence. An enhancer element is any nucleic acid molecule that increases transcription of a nucleic acid molecule when functionally linked to a promoter regardless of its relative position. An enhancer may be an innate element of the promoter or a heterologous element inserted to enhance the amount of promotor activity or tissue-specificity of a promoter.

Various enhancers may be used including introns with gene expression enhancing properties in plants (US Patent Application Publication Number 2009/0144863), the ubiquitin intron (i.e., the maize ubiquitin intron 1 (see, for example, NCBI sequence S94464)), the omega enhancer or the omega prime enhancer (Gallie, et al., (1989) Molecular Biology of RNA ed. Cech (Liss, New York) 237-256 and Gallie, et al., (1987) Gene 60:217-25), the CaMV 35S enhancer (see, e.g., Benfey, et al., (1990) EMBO J. 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

A repressor (also sometimes called herein silencer, repressor element, or repressor binding element) is defined as any nucleic acid molecule which inhibits the transcription when functionally linked to a promoter regardless of relative position.

"Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

The termination region may be native with the transcriptional initiation region, may be native with the operably linked DNA sequence of interest, may be native with the plant host or may be derived from another source (i.e., foreign or heterologous to the promoter, the sequence of interest, the plant or any combination thereof).

The sequences include one or more contiguous nucleotides "Contiguous nucleotides" is used herein to refer to nucleotide residues that are immediately adjacent to one another.

As used herein non-genomic nucleic acid sequence, nucleic acid molecule or polynucleotide refers to a nucleic acid molecule that has one or more changes in the nucleic acid sequence compared to a native or genomic nucleic acid sequence. In some embodiments, the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence.

Provided are polypeptides having at least about or at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to polypeptides referenced in the sequence listing, as well as amino acid substitutions, deletions, insertions, fragments thereof, and combinations thereof. The term "about" when used herein in context with percent sequence identity means +/−0.5%. These values can be appropriately adjusted to determine corresponding homology of proteins considering amino acid similarity and the like.

In some embodiments, the sequence identity is against the full-length sequence of a polypeptide disclosed in the sequence listing. In some embodiments, the polypeptide retains activity or shows enhanced or reduced activity As used herein, the term "protein," "peptide molecule," or "polypeptide" includes those molecules that undergo modification, including post-translational modifications, such as, but not limited to, disulfide bond formation, glycosylation, phosphorylation or oligomerization.

The terms "amino acid" and "amino acids" refer to all naturally occurring L-amino acids.

Variants may be made by making random mutations or the variants may be designed. In the case of designed mutants, there is a high probability of generating variants with similar activity to the native polypeptide when amino acid identity is maintained in critical regions of the polypeptide which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 2 provides a listing of examples of amino acids belonging to each class.

TABLE 2

Classes of amino acids

| Class of Amino Acid | Examples of Amino Acids |
| --- | --- |
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

Alternatively, alterations may be made to the protein sequence of many proteins at the amino or carboxy terminus without substantially affecting activity. This can include insertions, deletions or alterations introduced by modern molecular methods, such as polymerase chain reaction (PCR), including PCR amplifications that alter or extend the protein coding sequence by inclusion of amino acid encoding sequences in the oligonucleotides utilized in the PCR amplification. Alternatively, the protein sequences added can include entire protein-coding sequences, to generate protein fusions. Such fusion proteins are often used to (1) increase expression of a protein of interest (2) introduce a binding domain, enzymatic activity or epitope to facilitate either protein purification, protein detection or other experimental uses (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence. The percent identity between two sequences can be determined using techniques similar to those described below, with or without allowing gaps. In calculating percent identity, typically exact matches are counted. A gap, (a position in an alignment where a residue is present in one sequence but not in the other) is regarded as a position with non-identical residues.

The determination of percent identity between two sequences can be accomplished using a mathematical algorithm. A non-limiting example of a mathematical algorithm utilized for the comparison of two sequences is the algorithm incorporated into the BLASTN and BLASTX programs. Karlin and Altschul (1990) *Proc. Nat'l. Acad. Sci. USA* 87:2264, Altschul et al. (1990) *J. Mol. Biol.* 215:403, and Karlin and Altschul (1993) *Proc. Nat'l. Acad. Sci. USA* 90:5873-5877. BLAST nucleotide searches can be performed with the BLASTN program, score=100, word length=12, to obtain nucleotide sequences homologous to nucleic acid molecules disclosed herein. BLAST protein searches can be performed with the BLASTX program, score=50, word length=3, to obtain amino acid sequences homologous to polypeptides disclosed herein. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4(1):11-17. Such an algorithm is incorporated into the ALIGN program (version 2.0), which is part of the GCG Wisconsin Genetics Software Package, Version 10 (available from Accelrys, Inc., San Diego, Calif., USA). When utilizing the ALIGN program for comparing amino acid sequences, a PAM120 weight residue table, a gap length penalty of 12, and a gap penalty of 4 can be used. Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Isolated or recombinant nucleic acid molecules comprising nucleic acid sequences encoding reticulon-like or trehalose-6-phoshate synthase polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences that encode reticulon-like or trehalose-6-phoshate synthase polypeptides, variants and truncations, may be synthesized and cloned into standard plasmid vectors by conventional means, or may be obtained by standard molecular biology manipulation of other constructs containing the nucleotide sequences.

In some embodiments, plants, plant parts, plant cells, seeds and methods of making and using thereof include a genome modified to contain a deletion. An example of such a deletion is the CR1/CR3 deletion line #1 which contains a 20,117 base pair (bp) deletion corresponding to the sequence beginning at position 2268 and ending at 22,384 of SEQ ID NO 11. Plants, seeds, plant parts and plant cell comprising this deletion and methods of making such plants, seeds, plant parts and plant cells are provided.

In some embodiments, the nucleic acid molecule is a polynucleotide having the sequence set forth in SEQ ID NO: 1, 3, 5, 7, 9 or 11 and variants, fragments and complements thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In some embodiments, the nucleic acid molecule encoding the polypeptide is a non-genomic nucleic acid sequence.

In some embodiments, the nucleic acid molecule encoding a polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, wherein the encoded polypeptide is functional to increase protein in a soybean seed.

In some embodiments, the polynucleotide encodes a polypeptide having, or the polypeptide has, at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, 4, 6, 8, or 10 and optionally has at least one amino acid substitution, deletion, insertion or combination therefore, compared to the native sequence.

In some embodiments, the nucleic acid molecule encodes a polypeptide comprising, or the polypeptide comprises, an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2, 4, 6, 8, or 10.

In some embodiments, the nucleic acid encodes a polypeptide having or the polypeptide has, at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2. In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

The embodiments also encompass nucleic acid molecules encoding reticulon-like or trehalose-6-phoshate synthase polypeptides variants. "Variants" of the polypeptide encoding nucleic acid sequences include those sequences that encode the polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the polypeptides disclosed as discussed below.

Oligonucleotide probes and methods for detecting the polynucleotides described herein are provided. Oligonucleotide probes are detectable nucleotide sequences, such as by an appropriate radioactive label or may be fluorescence as described in, for example, U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying modified genes of reticulon-like or trehalose-6-phoshate synthase polypeptides, which modified genes and methods are provided. The nucleotide segments which are used as probes can be synthesized using a DNA synthesizer and standard procedures. These nucleotide sequences can also be used as PCR primers to amplify genes.

As is well known to those skilled in molecular biology, similarity of two nucleic acids can be characterized by their tendency to hybridize. Provided are nucleic acids that hybridize to those sequences disclosed herein under stringent conditions. As used herein the terms "stringent conditions" or "stringent hybridization conditions" are intended to refer to conditions under which a probe or nucleic acid will hybridize (anneal) to a particular sequence to a detectably greater degree than to other sequences (e.g. at least 2-fold over background).

Provided are nucleotide constructs comprising sequences described herein. The use of the term "nucleotide constructs" herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

Provided are plants, plant cells, plant seeds and plant nuclei that are modified by gene editing. In some embodiments, gene editing may be facilitated through the induction of a double-stranded break (DSB) or single-strand break, in a defined position in the genome near the desired alteration. DSBs can be induced using any DSB-inducing agent available, including, but not limited to, TALENs (transcription activator-like effector nucleases), meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template. In some embodiments, the methods do not use TALENs enzymes or technology and plants and seeds are produced from methods which do not use TALENs enzymes or technology.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 *Nature Methods* Vol. 10: 957-963.)

The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLI-DADG, GIY-YIG, H-N-H, and His-Cys box families. These motifs participate in the coordination of metal ions and hydrolysis of phosphodiester bonds.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site.

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

Provided are plants, plant cells, plant seeds and plant nuclei that are transformed with sequences described herein.

Transformation may be stable or transient. "Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation methods include introduction of a recombinant DNA construct comprising an expression cassette. Provided are constructs which include one or more heterologous promoter sequences operably connected to one or more polynucleotides encoding polypeptides disclosed herein and appropriate transcription termination sequences and plants, seeds, cells and nuclei containing the recombinant DNA construct or expression cassette.

Transformation methods include introduction of a suppression DNA construct or a construct that results in increased expression of a target gene, such as encoding the reticulon-like or trehalose-6-phoshate synthase polypeptides. "Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

The embodiments further relate to plant-propagating material of a transformed plant of the embodiments including, but not limited to, seeds, tubers, corms, bulbs, leaves and cuttings of roots and shoots. Methods of plant breeding by crossing a modified plant described herein with a second different plant are provided. Progeny plants, plant cells, seeds and plant nuclei from such breeding methods are provided, such as F1 progeny plants, plant cells, seeds and plant nuclei.

Transformation of any plant species can be carried out, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

The methods comprise providing a plant or plant cell expressing a polynucleotide encoding the polypeptide sequence disclosed herein and growing the plant or a seed thereof in a field. In some embodiments, the expression of the modified polypeptide results in a plant producing increased yield or biomass.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the modified sequence.

Methods of detecting the modified polynucleotides are provided. Methods of extracting modified DNA from a sample or detecting the presence of DNA corresponding to the modified genomic sequences comprising deletions, such as Deletion #1 or Deletion #3 depicted in FIG. 1 or the deletion junction sequence of Deletion #1 (FIG. 1) shown in SEQ ID NO: 19 can be carried out. SEQ ID NO: 19 contains a feature following position 24, which feature can be any number of nucleotides from 0 to 45, and if present, the nucleotide can be A, G, C or T. For example, the 45 "n" at positions 25-69 of SEQ ID NO: 19 can be entirely absent or a length of 0 to 1, 0 to 2, 0 to 3, 0 to 4, 0 to 5, Oto 10, Oto 15, 0 to 20, 0 to 25, 0 to 30, 0 to 35, 0 to 40, or 0 to 45 nucleotides, and when present may contain any combination of C, T, G or A. Such methods of detecting polynucleotides comprise contacting a sample comprising soybean genomic DNA with a DNA primer set, that when used in a nucleic acid amplification reaction, such as the polymerase chain reaction (PCR), with genomic DNA extracted from soybeans produces an amplicon that is diagnostic for either the presence or absence of the deleted sequence, reticulon-like coding sequence or trehalose-6-phosphate synthase coding sequence. The methods include the steps of performing a nucleic acid amplification reaction, thereby producing the amplicon and detecting the amplicon.

In some embodiments one of the pair of DNA molecules comprises the wild type sequence where the modification occurs with the second of the pair being upstream or downstream as appropriate and suitably in proximity to the wild type sequence where the modification occurs, such that an amplicon is produced when the wild type sequence is present, but no amplicon is produced when the deletion is present. In the context of the methods, in proximity means sufficiently close such that the distance between the first and second of the pair of DNA molecules facilitates the production of an amplicon when included in a DNA amplification reaction comprising soybean genomic DNA. For example, the second primer may bind at a location beginning at, within or less than 1, 2, 5, 10, 20, 30, 40, 50, 60, 70, 80, 90, 100, 150, 200, 250, 300, 350, 400, 450, 500, 600, 700, 800, 900, 1000, 1500, 16, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500 or 10000 nucleotides upstream or downstream of the end of the binding site of the first DNA primer molecule.

Probes and primers are provided which are of sufficient nucleotide length to bind specifically to the target DNA sequence under the reaction or hybridization conditions. Suitable probes and primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 2, 5 2, 4 23, 22, 21, 20, 19, 18, 17, 16, 15, 14, 13, or 12 nucleotides in length. Such probes and primers can hybridize specifically to a target sequence under high stringency hybridization conditions. Preferably, probes and primers have complete or 100% DNA sequence similarity of contiguous nucleotides with the target sequence, although probes which differ from the target DNA sequence but retain the ability to hybridize to target DNA sequence may be also be used. Reverse complements of the primers and probes disclosed herein are also provided and can be used in the methods and compositions described herein.

In some embodiments, one of the pair of DNA molecules comprises the modification or traverses the modification junction, such as the deletion junction at position 24 to position 26 of SEQ ID NO: 19 (which junction may include from 0 to 45 nucleotides between position 24 and 26 of SEQ ID NO: 19), with the second DNA molecule of the pair being upstream or downstream of the genomic sequence as appropriate, such that an amplicon is produced when the modified allele is present, but no amplicon is produced when the wild type allele is present. Suitable primers for use in reactions to detect the presence of the modified alleles can be designed based on the junction sequences described herein. In some embodiments, the first or second primer molecule binds to a sequence corresponding to position 1 to position 2268 of SEQ ID NO: 11, or a complement thereof, or to a sequence corresponding to position 22,384 to position 24,650 of SEQ ID NO: 11, or a complement thereof. In some embodiments, the primers bind to the target sequence to produce an amplicon of a length described herein. The amplicon molecule produced can be at least 5, 10, 15, 20, 25, 30, 35, 40, 41, 42, 43, 44, 45, 46, 47, 48, 49, 50, 60, 70, 80, 90, 100, 125, 150, 175, 200, 225, 250, 275, 300, 350, 400, 450, 500, 550, 600, 650, 700, 750, 800, 850, 900, 950, 1000, 1500 or 2000 nucleotides in length and less than about 10000, 9000, 8000, 7500, 7000, 6500, 6000, 5500, 5000, 4500, 4000, 3500, 3000, 2500, 2000, or 1500 nucleotides in length.

The foregoing invention has been described in detail by way of illustration and example for purposes of clarity and understanding. As is readily apparent to one skilled in the art, the foregoing disclosures are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

All publications, patents, and patent applications mentioned in the specification are incorporated by reference herein for the purpose cited to the same extent as if each was specifically and individually indicated to be incorporated by reference herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present).

The following examples illustrate particular aspects of the disclosure and are not intended in any way to limit the disclosure.

EXAMPLES

Example 1. Fine Mapping of Causative Gene in High Protein Mutants from Fast Neutron Mutagenesis in Soybean Protein is the most valuable component in soybean seed. One high protein/low oil mutant line (Po1) was identified from a fast neutron mutant population (Bolon et al. 2011 Phenotypic and genomic analysis of a fast neutron mutant population resource in soybean. Plant Physiol 156:240-253). The Pot mutant was mapped to a 39 Kb deletion on chromosome 10 which contains three possible candidate genes. The causative gene, however, was not identified due to no recombination in deletion region. CRISPR/CAS9 was used to create three overlapping deletions in this region to identify the causative gene responsible for high protein/low oil content (FIG. 1).

Six guide RNAs (gRNAs) targeting specific sites in the region of interests were designed as shown in Table 3. The genomic sequence of this region in wild-type soybean is shown in SEQ ID NO: 11. Each pair of gRNAs and CAS9 were delivered to soybean by transformation. T0 plants with heterozygous CR1/CR3 deletion #1 and CR4/CR6 deletion #3 were identified based on molecular analysis of variants. T1 seeds from selfed T0 plants were segregating for 1:2:1 of homozygous deletion, heterozygous deletion and wild type.

TABLE 3

Guide RNA designed to produce deletions in region of interest

| Edit designation (guide pair) | Approximate expected deletion size (bp) | Guide 1 name | Guide 1 sequence | Guide 2 name | Guide 2 sequence |
|---|---|---|---|---|---|
| GM-HP-CR1/CR3 | 20,118 | GM-HP-CR1 (SEQ ID NO: 12) | GGAAAGCTT AAATGAAACA T | GM-HP-CR3 (SEQ ID NO: 13) | GTGTGCCCC TTGTCAGTT GT |

TABLE 3-continued

Guide RNA designed to produce deletions in region of interest

| Edit designation (guide pair) | Approximate expected deletion size (bp) | Guide 1 name | Guide 1 sequence | Guide 2 name | Guide 2 sequence |
|---|---|---|---|---|---|
| GM-HP-CR2/CR5 | 25,988 | GM-HP-CR2 (SEQ ID NO: 14) | GTTAGACGA AAAACCATAT G | GM-HP-CR5 (SEQ ID NO: 15) | GGTGCGAAC CTATTTCAAC T |
| GM-HP-CR4/CR6 | 26,957 | GM-HP-CR4 (SEQ ID NO: 16) | GCCAAGGCA ATTGACACAT A | GM-HP-CR6 (SEQ ID NO: 17) | GATCGCGCA GGATGAGTA GA |
| | | GM-RET-CR1 (SEQ ID NO: 18) | GTGGCCTCT GTGCAGTTT CA | | |

Figure 2:
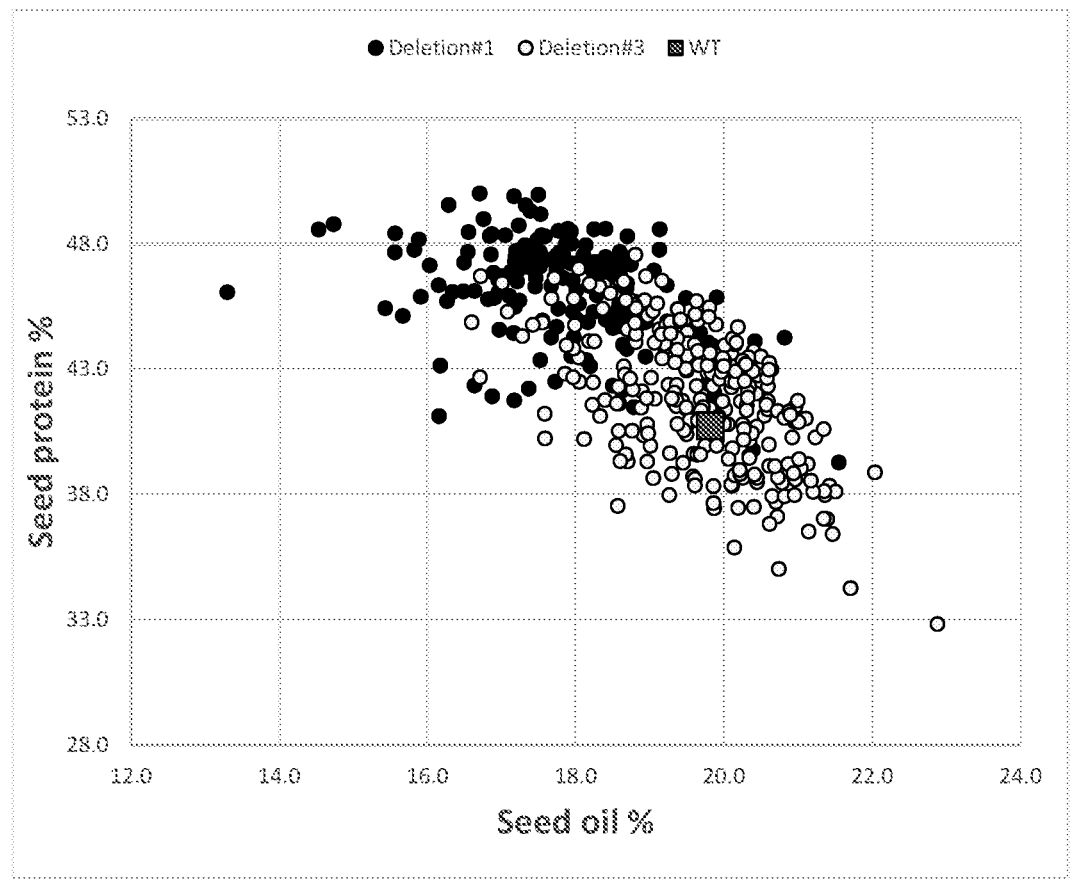
FIG. 2 is graph showing the protein content of T1 seeds from the CR1/CR3 deletion line #1 (Deletion #1) and CR4/CR6 deletion line #3 (Deletion #3) compared with wild-type (WT).

T1 seeds protein and oil content were determined by the single seed NIR as described previously (Roesler et al. 2016, Plant Physiol. 171(2):878-93). T1 seeds from CR1/CR3 deletion #1 line showed an increase in protein content and a decrease in oil content as compared to T1 seeds from CR4/CR6 deletion #3 line and wild type average, indicating that the deleted fragment in CR1/CR3 deletion #1 line contains the causative gene for high protein/low oil (FIG. 2).

T2 seeds were obtained from selfing CR1/CR3 deletion #1 line. T2 seed oil and protein content were determined by FT-NIR as described previously (Roesler et al. 2016, Plant Physiol. 171(2):878-93) and expressed by weight on a 13% moisture basis. Two plants showed significant increases in seed protein content and protein+oil (PROIL) content (Table 4).

TABLE 4

T2 seed protein and oil content

| T2 | Oil % | Protein % | Oil + Protein % |
|---|---|---|---|
| plant1 | 19.9 | 37.7 | 57.6 |
| plant2 | 19.7 | 39.3 | 59 |
| 93Y21 WT | 21.7 | 34.8 | 56.5 |

The CR1/CR3 deletion line #1 contains a 20,117 bp deletion starting at position 2268 and ending at 22,384 of SEQ ID NO 11. Sequence analysis of the deletion #1 region identified two potential genes, Glyma.10g270800 and Glyma.10g270900. The high protein phenotype was identified as being caused by deletion of either glyma.10g270800, glyma.10g270900 or both. Glyma.10g270800 encodes a trehalose-6-phosphate synthase which catalyzes the first step in trehalose synthesis and plays a role in regulating stress response, sugar sensing, growth and development. Glyma.10g 270900 encodes a reticulon-like protein containing a reticulon homology domain. Reticulons are a group of proteins found predominantly in endoplasmic reticulum, playing a role in promoting ER membrane curvature. Both oil and protein are synthesized in ER, such that a change of ER membrane structure may regulate protein and oil biosynthesis. Unlike CR1/CR3 deletion line #1, CR4/CR6 deletion line #3 did not show any significant changes in protein and oil content in seeds. Therefore, glyma.10g271200 (SEQ ID NO: 9), encoding a wall-associated receptor kinase (SEQ ID NO: 10), glyma.10g271000 (SEQ ID NO: 5), and glyma.10g271100 (SEQ ID NO: 7), which are found in the deletion region of the CR4/CR6 deletion line #3 are unlikely the causative genes for high protein phenotype.

Example 2: Validation of Glyma.10g270900 and Glyma.10g270800 as the Causative Gene for High Protein Phenotype To validate that glyma.10g270900 is the causative gene for high protein phenotype, guide RNAs were designed in the exon1 of the Glyma.10g270900 to knockout out the reticulon-like protein. The reticulon-like knockout line is expected to show a high protein phenotype, validating that the reticulon-like protein is involved in regulating protein and oil content in soybean seed. Knockout of reticulon-like gene in elite soybean by CRISPR/cas9 is expected increased seed protein content.

Similarly, guide RNAs were designed to knockout glyma.10g270800. Knockout of trehalose-6-P synthase may lead to high protein content, implicating glyma.10g270800 as the causative gene, either alone or if not alone, in combination with knockout of the reticulon-like polypeptide.

Example 3. Genome Editing of Reticulon-Like Protein for Increasing Protein Content in Soybean For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) Proc. Natl. Acad. Sci. USA 109: E2579-86, Jinek et al. (2012) Science 337:816-21, Mali et al. (2013) Science 339:823-26, and Cong et al. (2013) Science 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into said target site.

To use the guide RNA/Cas endonuclease system in soybean, the Cas9 gene from *Streptococcus pyogenes* M1 GAS (SF370) was soybean codon optimized per standard techniques known in the art. To facilitate nuclear localization of the Cas9 protein in soybean cells, Simian virus 40 (SV40) monopartite amino terminal nuclear localization signal (MAPKKKRKV) and *Agrobacterium tumefaciens* bipartite VirD2 T-DNA border endonuclease carboxyl terminal nuclear localization signal (KRPRDRHDGELGGRKRAR) were incorporated at the amino and carboxyl-termini of the Cas9 open reading frame, respectively. The soybean optimized Cas9 gene was operably linked to a soybean constitutive promoter such as the strong soybean constitutive promoter GM-EF1A2 (US patent application 20090133159) or regulated promoter by standard molecular biological techniques.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in soybean, the soybean U6 polymerase III promoter and U6 polymerase III terminator were used.

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter for example, GM-U6-13.1 promoter or GM-U6-9.1 promoter, to express guide RNA to direct Cas9 nuclease to designated genomic site. The guide RNA coding sequence was 76 bp long and comprised a 20 bp variable targeting domain from a chosen soybean genomic target site on the 5' end and a tract of 4 or more T residues as a transcription terminator on the 3' end. The first nucleotide of the 20 bp variable targeting domain was a G residue to be used by RNA polymerase III for transcription. Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct.

To validate that glyma.10g270800 is the causative gene for high protein phenotype, a guide RNA (GM-RET-CR1) was designed in the exon1 of the Glyma.10g270900 to knockout out the reticulon-like protein (Table 3). The soybean U6 small nuclear RNA promoter, GM-U6-13.1 promoter, was used to express guide RNAs to direct Cas9 nuclease to designated genomic target sites. A soybean codon optimized Cas9 endonuclease expression cassette and guide RNA expression cassettes were linked in the plasmid (RV029967). The RV029967 construct, which contains the GM-RET-CR1 gRNA expression cassette and Cas9 expression cassette, was made to knockout the Reticulon-like gene in elite soybean line. The construct was transformed into *Ochrobactrum haywardense* H1-8 strain for soybean transformation.

*Ochrobactrum*-mediated soybean embryonic axis transformation is done essentially as described in US Patent application US 2018/0216123 A1. Mature dry seeds of soybean cultivar 93Y21 are disinfected using chlorine gas and imbibed on semi-solid medium containing 5 g/l sucrose and 6 g/l agar at room temperature in the dark. After an overnight incubation, the seed is soaked in distilled water for an additional 3-4 hrs at room temperature in the dark. Intact embryonic axis is isolated from cotyledon using a scalpel blade in distilled sterile water. The embryonic axis explants are transferred to the deep plate with 15 mL of *Ochrobactrum haywardense* H1-8 further containing a helper vector PHP85634 (RV005393) with binary vector RV029968 or RV029969 with suspension at OD600=0.5 in infection medium containing 200 μM acetosyringone. The plates are sealed with parafilm ("Parafilm M" VWR Cat #52858), then sonicated (Sonicator-VWR model 50T) for 30 seconds. After sonication, embryonic axis explants are transferred to a single layer of autoclaved sterile filter paper (VWR #415/Catalog #28320-020). The plates are sealed with Micropore tape (Catalog #1530-0, 3M, St. Paul, Minn.)) and incubated under dim light (5-10 μE/m$^2$/s, cool white fluorescent lamps) for 16 hrs at 21° C. for 3 days.

After co-cultivation, the embryonic axis explants are cultured on shoot induction medium solidified with 0.7% agar in the absence of selection. The base of the explant (i.e., root radical of embryonic axis) is embedded in the medium. Shoot induction is carried out in a Percival Biological Incubator at 26° C. with a photoperiod of 18 hrs and a light intensity of 40-70 μE/m$^2$/s. 6 to 7 weeks after transformation, elongated shoots (>1-2 cm) are isolated and transferred to rooting medium containing selection agent. Transgenic plantlets are transferred to soil pots and were grown in the greenhouse.

Genomic DNA is extracted from soybean samples and analyzed by regular PCR. PCR primers are designed to amplify the genomic region of interests. The PCR bands are cloned into pCR2.1 vector using a TOPO-TA cloning kit (Invitrogen) and multiple clones are sequenced to check for target site sequence changes as the results of NHEJ. The frameshift knockout variants by the GM-RET-CR1 can be identified. Screening of seed from edited events are performed using non-destructive single seed Near Infrared analysis (SS-NIR) to evaluate protein contents and other seed compositions. Knockout of reticulon-like gene in elite soybean by CRISPR/cas9 should increase seed protein content. If the reticulon-like knockout line shows high protein phenotype, this will validate that reticulon-like protein is involved in regulating protein and oil content in soybean seed.

What is claimed is:

1. A soybean seed comprising modifications that increase protein content in the soybean seed, the soybean seed comprising a modification selected from a deletion, insertion or substitution of nucleotides in both (i) a genomic sequence encoding a reticulon-like polypeptide comprising an amino acid sequence that is at least 95% identical to SEQ ID NO: 2 and (ii) a genomic sequence encoding a trehalose-6-phosphate synthase polypeptide comprising an amino acid sequence that is at least 95% identical to SEQ ID NO: 4, the modification resulting in suppression of the activity of the reticulon-like polypeptide and the trehalose-6-phosphate synthase polypeptide, wherein the soybean seed comprising the modifications has an oil content of at least 15% by weight and an increased protein content relative to a control soybean seed not comprising the modifications resulting in suppression of the activity of the reticulon-like polypeptide and the trehalose-6-phosphate synthase polypeptide.

2. The seed of claim 1, wherein the seed comprises on chromosome 10 a polynucleotide encoding a wall-associated receptor kinase comprising an amino acid sequence that is at least 95% identical to SEQ ID NO: 10.

3. The seed of claim 1, wherein the modifications comprise a deletion or insertion in a coding sequence or a transcription regulatory region of the genomic sequence of the reticulon-like polypeptide and the trehalose-6-phosphate synthase polypeptide.

4. The seed of claim 1, wherein the seed has a 1 percentage point increase by weight of PROIL at 13% moisture relative to a control seed not comprising the modifications.

5. The seed of claim 1, wherein the PROIL content of the seed is at least 55% by weight.

6. The seed of claim 1, further comprising a heterologous nucleic acid sequence selected from the group consisting of: a reporter gene, a selection marker, a disease resistance gene, a herbicide resistance gene, an insect resistance gene, a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants.

7. A method of plant breeding comprising crossing a plant grown from the seed of claim 1 with a second soybean plant to produce progeny seed.

8. The seed of claim 3, wherein the deletion or insertion results in a frame-shift of the genomic sequence encoding the reticulon-like polypeptide.

9. The seed of claim 3, wherein the deletion or insertion results in a frame-shift of the genomic sequence encoding the trehalose-6-phosphate synthase polypeptide.

10. The seed of claim 1, wherein the modification comprises a substitution of nucleotides in the genomic sequence encoding the reticulon-like polypeptide.

11. The seed of claim 1, wherein the modification comprises a substitution of nucleotides in the genomic sequence encoding the trehalose-6-phosphate synthase polypeptide.

12. A plant grown from the seed of claim 1, wherein the plant comprises the modifications resulting in suppression of the activity of the reticulon-like polypeptide and the trehalose-6-phosphate synthase polypeptide.

13. The plant of claim 12, wherein the plant produces seeds having an oil content of at least 15% by weight.

14. The plant of claim 12, wherein the plant has a similar or increased yield of seeds, relative to a control plant not comprising the modifications.

15. A method for producing high protein meal, the method comprising processing seeds harvested from the plant of claim 12 to produce the high-protein meal, wherein the seeds harvested comprise the modifications.

* * * * *

SEQUENCE LISTING

<160> NUMBER OF SEQ ID NOS: 19

<210> SEQ ID NO 1
<211> LENGTH: 639
<212> TYPE: DNA
<213> ORGANISM: Glycine max

<400> SEQUENCE: 1

```
atgccaatcc gttcccgtga aactgcacag aggccaggat tgttagaccg tcaaagacca      60
ctacatgcag tccttggcgg aggaaagctt gctgatatat tgctatggaa agacaagata     120
ttatcggcag caatggtagc agggttctcc atcatttggt tcctctttga agtggtcgaa     180
tacaattttc ttactctact tgtcacatc ctcatggccg ttatgctcat cctattcgta      240
tggtataatg cagctggact tatcacatgg aacctgccac aaatctatga ttttcaaatc     300
cccgaaccca cctttagatt cttgtttcaa agctcaact cgttcttaag gagattttac      360
gacatttcaa ctgggaaaga cctcacactc ttctttgtga caattgcgtg tctctggatc     420
ttatcagcta ttgggaatta ttttaccact ttgaatcttc tatatatcat gttcctctgc     480
ctggtgactc ttcccattat gtatgagaga tatgaatatg aggtgaatta ctagcaagc      540
aaaggaaacc aagacgtgca gagattgttc aacacattgg atactaaagt tctaaccaag     600
attccaaggg gacctgtgaa agaaaagaag aagaaatga                           639
```

<210> SEQ ID NO 2
<211> LENGTH: 212
<212> TYPE: PRT
<213> ORGANISM: Glycine max

<400> SEQUENCE: 2

```
Met Pro Ile Arg Ser Arg Glu Thr Ala Gln Arg Pro Gly Leu Leu Asp
1               5                   10                  15

Arg Gln Arg Pro Leu His Ala Val Leu Gly Gly Gly Lys Leu Ala Asp
            20                  25                  30

Ile Leu Leu Trp Lys Asp Lys Ile Leu Ser Ala Ala Met Val Ala Gly
        35                  40                  45

Phe Ser Ile Ile Trp Phe Leu Phe Glu Val Val Glu Tyr Asn Phe Leu
    50                  55                  60

Thr Leu Leu Cys His Ile Leu Met Ala Val Met Leu Ile Leu Phe Val
65                  70                  75                  80

Trp Tyr Asn Ala Ala Gly Leu Ile Thr Trp Asn Leu Pro Gln Ile Tyr
                85                  90                  95

Asp Phe Gln Ile Pro Glu Pro Thr Phe Arg Phe Leu Phe Gln Lys Leu
            100                 105                 110

Asn Ser Phe Leu Arg Arg Phe Tyr Asp Ile Ser Thr Gly Lys Asp Leu
        115                 120                 125

Thr Leu Phe Phe Val Thr Ile Ala Cys Leu Trp Ile Leu Ser Ala Ile
    130                 135                 140

Gly Asn Tyr Phe Thr Thr Leu Asn Leu Leu Tyr Ile Met Phe Leu Cys
145                 150                 155                 160

Leu Val Thr Leu Pro Ile Met Tyr Glu Arg Tyr Glu Tyr Glu Val Asn
                165                 170                 175

Tyr Leu Ala Ser Lys Gly Asn Gln Asp Val Gln Arg Leu Phe Asn Thr
            180                 185                 190

Leu Asp Thr Lys Val Leu Thr Lys Ile Pro Arg Gly Pro Val Lys Glu
        195                 200                 205

Lys Lys Lys Lys
    210
```

<210> SEQ ID NO 3
<211> LENGTH: 2562
<212> TYPE: DNA
<213> ORGANISM: Glycine max

<400> SEQUENCE: 3

```
atggtttcaa ggtcatattc taacttgtta gatcttactt cttgtggctc cccgactttc      60
agtcgtgaga agaaaaggct ccctcgagtg gcaactgttg ctggagtact gtctgaatta     120
gatgatgaaa ccagcaacag tgtttgctct gatactccat cctcagtctc tcaagagagg     180
atgatcattg ttggtaacca gcttccatta aaggcacaca gaaaagacaa cggtacttgg     240
gagttcacat gggatgagga ctcacttctt ttacagctga agatggtct tggggatgat      300
gtggaaacta tctatattgg ttgtcttaaa gaagagattg agccaagtga gcaagatgat     360
gttgctctgt acttgcttga cactttcaaa tgtgtgccaa cgttcctccc tcctgagctt     420
tttagtaaat tctatcatgg attctgcaaa caacatctat ggcctttgtt tcactacatg     480
cttcccctgt cacctgatct tggtggtcga ttcgataggt ccctttggca agcttacctt     540
tctgtgaaca agatatttgc ggataaagtg atggaagtca tcagccctga tgatgacttt     600
gtgtgggttc atgactacca tctgatggta cttcctacat ttttgagaaa gagatttaac     660
agggtgaggc taggattctt cctccatagt ccatttcctt cgtctgagat ataccgaacc     720
cttcctgtta gggatgaact tcttagagct cttctgaatt ctgaccttat tgggtttcat     780
acttttgatt atgccaggca tttcctctcc tgttgcagca gaatgcttgg gatttcttac     840
caatccaagc gtggctacat tggccttgag tactatggaa gaacagtaag cattaagatt     900
cttcctgttg gtattcatat aggtcagctc caatctgtca tgagtcatcc cgagacagaa     960
agcaaggttg cagagttaaa aaaacagttc agagatcaaa ctgtgctgct cggggtggat    1020
gacatggata tcttcaaagg aatcagctta aaacttttgg ccatggaaca attgcttta    1080
caacatcctg ataagagggg cagagttgtt ctggtccaaa ttgctaaccc tgcaagaggc    1140
cgtggaaagg atgtgcagga ggtacaaagt gaaacttatg ccacgatgaa gaggataaat    1200
aatgcatttg gaaggcctgg atacacacct gtagtcttga ttgataacac acttcagagt    1260
tatgagcgaa ttgcttatta tgtgattgca gaatgttgcc ttgttacagc agtgagagat    1320
gggatgaacc ttatacccta tgaatatatc atttgtagac aaggaaatga gaagatagat    1380
gagattttag ggacagacct gcttactcaa aagaagagta tgctggtggt gtctgagttt    1440
attggctgct ccccttcgtt aagtggggca attcgagtga atccatggaa cattgattct    1500
gtcgctgaag ctatggattc tgcgttgatg gtcccagagg ctgaaaagca gatgcggcat    1560
gagaagcatt ataggtatgt tagtacacat gatgttgcgt attgggcacg tagcttcttg    1620
caggatctgg aaagggcatg tagagatcat ctgaggagga gatgctgggg aattggtttt    1680
ggtttaggct tccgagtgat tgctttggat ccaaacttta gaaagctatc tgtggaacat    1740
attgtttcag cttataagag gaccaagcac cgagcaattc ttttggatta tgatggcact    1800
atggtgcagc ctgggtcgat gagtttaaca cctaatgctg aagccgttag catcttgaac    1860
atcttgtgca gggacaccaa gaattgtgtt ttcattgtaa gtggaaggga gagaaagact    1920
cttactgaat ggtttttctt ctgtgaaagg atgggaatcg ctgcagagca tggttatttt    1980
gtgaggacaa atcgaaatgc agaatgggat acttgtattc cagtacctga ttttgagtgg    2040
aaacagattg ctgagccggt tatgcagtta tatatgaaa caactgatgg ttcaaacata    2100
gaggccaaag aaagtgctct agtttggaat tacgagtatg cagaccgaga ctttggttca    2160
tgccaagcta aggagctttt tgatcatctg gaaagtgttc ttgccaatga gcctgttttct    2220
gttaaaagta gtccaaacat tgttgaagtg aaacctcagg gtgtgagtaa gggtattgta    2280
```

-continued

```
gcagaacgtc ttctcttaac aatgcaacaa aagggagtgt ttccagattt tgttctatgc    2340
attggagatg acagatcaga cgaggacatg tttggggtaa tcatgaatgc aaaggcaacc    2400
ctatctccag ttgctgaagt gtttccatgc actgttggcc agaaacctag caaggcaaag    2460
tattatttgg aagacacaag tgagattttg agaatgttgc aaggccttgc caatgcttct    2520
gagcactcta ctagaacttc tttgcaacca gcttctcatt aa                       2562
```

<210> SEQ ID NO 4
<211> LENGTH: 853
<212> TYPE: PRT
<213> ORGANISM: Glycine max

<400> SEQUENCE: 4

```
Met Val Ser Arg Ser Tyr Ser Asn Leu Leu Asp Leu Thr Ser Cys Gly
1               5                   10                  15

Ser Pro Thr Phe Ser Arg Glu Lys Lys Arg Leu Pro Arg Val Ala Thr
            20                  25                  30

Val Ala Gly Val Leu Ser Glu Leu Asp Asp Glu Thr Ser Asn Ser Val
        35                  40                  45

Cys Ser Asp Thr Pro Ser Ser Val Ser Gln Glu Arg Met Ile Ile Val
    50                  55                  60

Gly Asn Gln Leu Pro Leu Lys Ala His Arg Lys Asp Asn Gly Thr Trp
65                  70                  75                  80

Glu Phe Thr Trp Asp Glu Asp Ser Leu Leu Gln Leu Lys Asp Gly
                85                  90                  95

Leu Gly Asp Asp Val Glu Thr Ile Tyr Ile Gly Cys Leu Lys Glu Glu
            100                 105                 110

Ile Glu Pro Ser Glu Gln Asp Val Ala Leu Tyr Leu Leu Asp Thr
        115                 120                 125

Phe Lys Cys Val Pro Thr Phe Leu Pro Pro Glu Leu Phe Ser Lys Phe
    130                 135                 140

Tyr His Gly Phe Cys Lys Gln His Leu Trp Pro Leu Phe His Tyr Met
145                 150                 155                 160

Leu Pro Leu Ser Pro Asp Leu Gly Gly Arg Phe Asp Arg Ser Leu Trp
                165                 170                 175

Gln Ala Tyr Leu Ser Val Asn Lys Ile Phe Ala Asp Lys Val Met Glu
            180                 185                 190

Val Ile Ser Pro Asp Asp Asp Phe Val Trp Val His Asp Tyr His Leu
        195                 200                 205

Met Val Leu Pro Thr Phe Leu Arg Lys Arg Phe Asn Arg Val Arg Leu
    210                 215                 220

Gly Phe Phe Leu His Ser Pro Phe Pro Ser Ser Glu Ile Tyr Arg Thr
225                 230                 235                 240

Leu Pro Val Arg Asp Glu Leu Leu Arg Ala Leu Leu Asn Ser Asp Leu
                245                 250                 255

Ile Gly Phe His Thr Phe Asp Tyr Ala Arg His Phe Leu Ser Cys Cys
            260                 265                 270

Ser Arg Met Leu Gly Ile Ser Tyr Gln Ser Lys Arg Gly Tyr Ile Gly
        275                 280                 285

Leu Glu Tyr Tyr Gly Arg Thr Val Ser Ile Lys Ile Leu Pro Val Gly
    290                 295                 300

Ile His Ile Gly Gln Leu Gln Ser Val Met Ser His Pro Glu Thr Glu
305                 310                 315                 320
```

```
Ser Lys Val Ala Glu Leu Lys Lys Gln Phe Arg Asp Gln Thr Val Leu
            325                 330                 335

Leu Gly Val Asp Asp Met Asp Ile Phe Lys Gly Ile Ser Leu Lys Leu
            340                 345                 350

Leu Ala Met Glu Gln Leu Leu Leu Gln His Pro Asp Lys Arg Gly Arg
            355                 360                 365

Val Val Leu Val Gln Ile Ala Asn Pro Ala Arg Gly Arg Gly Lys Asp
    370                 375                 380

Val Gln Glu Val Gln Ser Glu Thr Tyr Ala Thr Met Lys Arg Ile Asn
385                 390                 395                 400

Asn Ala Phe Gly Arg Pro Gly Tyr Thr Pro Val Val Leu Ile Asp Thr
                405                 410                 415

Pro Leu Gln Ser Tyr Glu Arg Ile Ala Tyr Tyr Val Ile Ala Glu Cys
                420                 425                 430

Cys Leu Val Thr Ala Val Arg Asp Gly Met Asn Leu Ile Pro Tyr Glu
            435                 440                 445

Tyr Ile Ile Cys Arg Gln Gly Asn Glu Lys Ile Asp Glu Ile Leu Gly
        450                 455                 460

Thr Asp Leu Leu Thr Gln Lys Lys Ser Met Leu Val Val Ser Glu Phe
465                 470                 475                 480

Ile Gly Cys Ser Pro Ser Leu Ser Gly Ala Ile Arg Val Asn Pro Trp
                485                 490                 495

Asn Ile Asp Ser Val Ala Glu Ala Met Asp Ser Ala Leu Met Val Pro
                500                 505                 510

Glu Ala Glu Lys Gln Met Arg His Glu Lys His Tyr Arg Tyr Val Ser
            515                 520                 525

Thr His Asp Val Ala Tyr Trp Ala Arg Ser Phe Leu Gln Asp Leu Glu
530                 535                 540

Arg Ala Cys Arg Asp His Leu Arg Arg Cys Trp Gly Ile Gly Phe
545                 550                 555                 560

Gly Leu Gly Phe Arg Val Ile Ala Leu Asp Pro Asn Phe Arg Lys Leu
                565                 570                 575

Ser Val Glu His Ile Val Ser Ala Tyr Lys Arg Thr Lys His Arg Ala
            580                 585                 590

Ile Leu Leu Asp Tyr Asp Gly Thr Met Val Gln Pro Gly Ser Met Ser
        595                 600                 605

Leu Thr Pro Asn Ala Glu Ala Val Ser Ile Leu Asn Ile Leu Cys Arg
    610                 615                 620

Asp Thr Lys Asn Cys Val Phe Ile Val Ser Gly Arg Glu Arg Lys Thr
625                 630                 635                 640

Leu Thr Glu Trp Phe Ser Ser Cys Glu Arg Met Gly Ile Ala Ala Glu
                645                 650                 655

His Gly Tyr Phe Val Arg Thr Asn Arg Asn Ala Glu Trp Asp Thr Cys
            660                 665                 670

Ile Pro Val Pro Asp Phe Glu Trp Lys Gln Ile Ala Glu Pro Val Met
        675                 680                 685

Gln Leu Tyr Met Glu Thr Thr Asp Gly Ser Asn Ile Glu Ala Lys Glu
    690                 695                 700

Ser Ala Leu Val Trp Asn Tyr Glu Tyr Ala Asp Arg Asp Phe Gly Ser
705                 710                 715                 720

Cys Gln Ala Lys Glu Leu Phe Asp His Leu Glu Ser Val Leu Ala Asn
                725                 730                 735
```

Glu Pro Val Ser Val Lys Ser Ser Pro Asn Ile Val Glu Val Lys Pro
                740                 745                 750

Gln Gly Val Ser Lys Gly Ile Val Ala Glu Arg Leu Leu Leu Thr Met
            755                 760                 765

Gln Gln Lys Gly Val Phe Pro Asp Phe Val Leu Cys Ile Gly Asp Asp
        770                 775                 780

Arg Ser Asp Glu Asp Met Phe Gly Val Ile Met Asn Ala Lys Ala Thr
785                 790                 795                 800

Leu Ser Pro Val Ala Glu Val Phe Pro Cys Thr Val Gly Gln Lys Pro
                805                 810                 815

Ser Lys Ala Lys Tyr Tyr Leu Glu Asp Thr Ser Glu Ile Leu Arg Met
            820                 825                 830

Leu Gln Gly Leu Ala Asn Ala Ser Glu His Ser Thr Arg Thr Ser Leu
        835                 840                 845

Gln Pro Ala Ser His
    850

<210> SEQ ID NO 5
<211> LENGTH: 588
<212> TYPE: DNA
<213> ORGANISM: Glycine max

<400> SEQUENCE: 5
atggcagttt ctgtaaccat tttagtcctc atcatcgctc tgcatctcat agccttcgtc      60
ttcgccgttg gcgccgaacg acgtcgtagc gaggccaaag tggtccccga cgagtacgac     120
gaccaaacct tctgccatta caccaccgac gcctccaccg tctacggcct ctccgccgtc     180
gccctcctcc tcctcagcca caccgtcctt aacggcgtca cgcgatgcct tgctgcggc      240 aaaggcctcg tctctggctg ctccgccacc tccgccgtca tctccttcat cctctcatgg     300
attagttttt tggcggcaga ggcgtgtctg ttagcagggt ctgcaaggaa tgcataccac     360
acaaagtaca gagggtattt tgtgaatcac gatttgtctt gtgctaccct acgcaagggt     420
gtgtttgctg ctggagctgc cttgaccttg ttgtccatgt tgaccgccat tttgtactat     480
tgggcacact ccaaggctga cactggtttc tgggagaagc accacaatga aggacttgga     540
ttggccacgc aacaccacca ccaaggtcct gactctgata aggcctga                  588

<210> SEQ ID NO 6
<211> LENGTH: 195
<212> TYPE: PRT
<213> ORGANISM: Glycine max

<400> SEQUENCE: 6

Met Ala Val Ser Val Thr Ile Leu Val Leu Ile Ile Ala Leu His Leu
1               5                   10                  15

Ile Ala Phe Val Phe Ala Val Gly Ala Glu Arg Arg Arg Ser Glu Ala
            20                  25                  30

Lys Val Val Pro Asp Glu Tyr Asp Asp Gln Thr Phe Cys His Tyr Thr
        35                  40                  45

Thr Asp Ala Ser Thr Val Tyr Gly Leu Ser Ala Val Ala Leu Leu Leu
    50                  55                  60

Leu Ser His Thr Val Leu Asn Gly Val Thr Arg Cys Leu Cys Cys Gly
65                  70                  75                  80

Lys Gly Leu Val Ser Gly Cys Ser Ala Thr Ser Ala Val Ile Ser Phe
                85                  90                  95

```
Ile Leu Ser Trp Ile Ser Phe Leu Ala Ala Glu Ala Cys Leu Leu Ala
            100                 105                 110

Gly Ser Ala Arg Asn Ala Tyr His Thr Lys Tyr Arg Gly Tyr Phe Val
        115                 120                 125

Asn His Asp Leu Ser Cys Ala Thr Leu Arg Lys Gly Val Phe Ala Ala
    130                 135                 140

Gly Ala Ala Leu Thr Leu Leu Ser Met Leu Thr Ala Ile Leu Tyr Tyr
145                 150                 155                 160

Trp Ala His Ser Lys Ala Asp Thr Gly Phe Trp Glu Lys His His Asn
                165                 170                 175

Glu Gly Leu Gly Leu Ala Thr Gln His His Gln Gly Pro Asp Ser
            180                 185                 190

Asp Lys Ala
        195

<210> SEQ ID NO 7
<211> LENGTH: 1206
<212> TYPE: DNA
<213> ORGANISM: Glycine max

<400> SEQUENCE: 7
atgttgggta ctgggttgaa cttcgggcgc gctcgcggcg aggatcggtt ctattctccg      60
gcaaaggctc gccggtcgct tctaactatg gagaatgaca agctgcgtag ggcccaaagc     120
gacgttgccg cgtctcgctc cgttagagac aaatcggtgg attcgggtaa ccggataccg     180
gagaaccggg tcgggtcgga cgaggcaaag aagagtggcg cggttccttc gtgtgaaccg     240
gtggcgaacc ggttgagtaa tctggagcgg ttcttgcagg cgatcacacc ctccgtgcct     300
gctcagtgtc tgcctaagag gacgacaaga ggactcaggg cgtgtggggc ggagtttcag     360
ccttacttcg ttctcgggga tttgtgggaa tcctttcggg aatggagtgc ttatggcgca     420
ggagtgccac ttgtactgaa tgacaaggat agtgttgttc agtactatgt tccgtatctg     480
tctgggatcc aaatttattc ccagaatgtg aagccaactg taaagtcaag gcaactgggg     540
gaggatagtg acagtgattt tagggactca agtagtgatg gtagcagtga tagtgaacct     600
gtacatggaa ggggattgag gaatcttccc catctgttag aagaggtgcc tcaatggatg     660
ggcggattat ctttgagaga ccaccattcc cttccaccag atgggttttc tagtgatgat     720
ggagaatctg tcaattctca gggttacttg attttgagt atcttgaacg ggaccctcct     780
tacagccgtg agcctttggc tgataagata atggatcttg cttttcaatt ccctgaactg     840 gtgacccta gaagttgtga tatactacca tcaagttgga tatctgtagc ctggtatcca     900
atttacagga taccaactgg tccaacatta aaagatctcg atgcttgttt tctgacatac     960
cattctcttt atatgcccat gggaggttca caaagagtcc aggctcccat gccacatcct    1020
actgagatgg acaatgtcca taaatgtct ttacctgttt ttggtcttgc ttcatataag    1080
ttcaaaggat ctctgtggac tcctaatggt ggacacgaat gccagcggtc tcttttgcag    1140
ggtgctgatg actggttaag actgcatcaa gtcagtcacc cagattttca gtttttcagc    1200
cgttga                                                               1206

<210> SEQ ID NO 8
<211> LENGTH: 401
<212> TYPE: PRT
<213> ORGANISM: Glycine max
```

<400> SEQUENCE: 8

```
Met Leu Gly Thr Gly Leu Asn Phe Gly Arg Ala Arg Gly Glu Asp Arg
1               5                   10                  15

Phe Tyr Ser Pro Ala Lys Ala Arg Arg Ser Leu Leu Thr Met Glu Asn
                20                  25                  30

Asp Lys Leu Arg Arg Ala Gln Ser Asp Val Ala Ala Ser Arg Ser Val
            35                  40                  45

Arg Asp Lys Ser Val Asp Ser Gly Asn Arg Ile Pro Glu Asn Arg Val
50                  55                  60

Gly Ser Asp Glu Ala Lys Lys Ser Gly Ala Val Pro Ser Cys Glu Pro
65                  70                  75                  80

Val Ala Asn Arg Leu Ser Asn Leu Glu Arg Phe Leu Gln Ala Ile Thr
                85                  90                  95

Pro Ser Val Pro Ala Gln Cys Leu Pro Lys Arg Thr Thr Arg Gly Leu
                100                 105                 110

Arg Ala Cys Gly Ala Glu Phe Gln Pro Tyr Phe Val Leu Gly Asp Leu
            115                 120                 125

Trp Glu Ser Phe Arg Glu Trp Ser Ala Tyr Gly Ala Gly Val Pro Leu
130                 135                 140

Val Leu Asn Asp Lys Asp Ser Val Val Gln Tyr Tyr Val Pro Tyr Leu
145                 150                 155                 160

Ser Gly Ile Gln Ile Tyr Ser Gln Asn Val Lys Pro Thr Val Lys Ser
                165                 170                 175

Arg Gln Leu Gly Glu Asp Ser Asp Ser Asp Phe Arg Asp Ser Ser Ser
            180                 185                 190

Asp Gly Ser Ser Asp Ser Glu Pro Val His Gly Arg Gly Leu Arg Asn
            195                 200                 205

Leu Pro His Leu Leu Glu Glu Val Pro Gln Trp Met Gly Gly Leu Ser
            210                 215                 220

Leu Arg Asp His His Ser Leu Pro Pro Asp Gly Phe Ser Ser Asp Asp
225                 230                 235                 240

Gly Glu Ser Val Asn Ser Gln Gly Tyr Leu Ile Phe Glu Tyr Leu Glu
                245                 250                 255

Arg Asp Pro Pro Tyr Ser Arg Glu Pro Leu Ala Asp Lys Ile Met Asp
            260                 265                 270

Leu Ala Phe Gln Phe Pro Glu Leu Val Thr Leu Arg Ser Cys Asp Ile
            275                 280                 285

Leu Pro Ser Ser Trp Ile Ser Val Ala Trp Tyr Pro Ile Tyr Arg Ile
            290                 295                 300

Pro Thr Gly Pro Thr Leu Lys Asp Leu Asp Ala Cys Phe Leu Thr Tyr
305                 310                 315                 320

His Ser Leu Tyr Met Pro Met Gly Gly Ser Gln Arg Val Gln Ala Pro
                325                 330                 335

Met Pro His Pro Thr Glu Met Asp Asn Val His Lys Met Ser Leu Pro
            340                 345                 350

Val Phe Gly Leu Ala Ser Tyr Lys Phe Lys Gly Ser Leu Trp Thr Pro
            355                 360                 365

Asn Gly Gly His Glu Cys Gln Arg Ser Leu Leu Gln Gly Ala Asp Asp
            370                 375                 380

Trp Leu Arg Leu His Gln Val Ser His Pro Asp Phe Gln Phe Phe Ser
385                 390                 395                 400

Arg
```

<210> SEQ ID NO 9
<211> LENGTH: 2583
<212> TYPE: DNA
<213> ORGANISM: Glycine max

<400> SEQUENCE: 9

| | | | | | |
|---|---|---|---|---|---|
| atggttttcc | aatccttaat | ctgtctatac | ccaatacatc | attcaccaaa | tatctacgaa | 60 |
| aatcagacac | ttcgagtgtc | caataccgcg | ttttcagttt | cacgaccaaa | caccaccaat | 120 |
| tccaaaggtt | gtcttcctct | tcctcttact | cagaatctca | ctcttcctag | tacccgcgag | 180 |
| ttcgatattg | ctccgaatca | aacagacatt | agattgttct | acggctgtgg | gtcattgcct | 240 |
| tggctggaag | agcacaaagt | tgggtgcttt | aacgaaacga | gttcagttct | ggcattgtat | 300 |
| aaagaggata | aaaatataag | ttttgtgtca | agaattgcc | agggcgaggt | tgtggatacg | 360 |
| atagtggaag | atggaataat | aggagggaat | gaagaagcgt | tgacaaaagg | gttttttgctg | 420 |
| acgtggaagg | ccggtaactg | cagcgtgtgc | acaacactg | agggaggtg | cttctgcact | 480 |
| gacagagttc | attctgccaa | atgtggtcct | gatgatgatc | cagaagttgt | ttttaggcag | 540 |
| acgtttagtt | tcacaagttc | acacagagac | agagagagta | ctagaaaact | gagaaatgag | 600 |
| gcccagaaat | ttgaagccac | tgattatgac | actgaacgcg | ttttctatct | ggcctcgttg | 660 |
| actggtcacg | ttgaagtgaa | gtgtgaacct | aaccgcttaa | aacgacatca | ccattcgtta | 720 |
| acgttgtcta | attgccttat | tatttcccac | actctttcaa | cgtcattcga | acgccccgac | 780 |
| tgtggctttt | tacccatacg | gaattgtgaa | gatccactca | agttcaaaat | gatccaatta | 840 |
| cagaataatg | agaatggtt | tcgggttgta | ctcgtagctc | agcttcggaa | cagttctatc | 900 |
| ataactttc | aaattagaga | caaacatctc | tatgaccttc | tgcagaacga | aagttgtgaa | 960 |
| gctttcagat | acaattatac | tattcctccc | ttctttcact | tgctgctttt | acgtatccaa | 1020 |
| taccacacaa | ctctgttcag | gtgcaaccgc | agcctccatg | tcagccctcc | cacgggcatg | 1080 |
| cttaattata | caaaatgccc | cgactacgat | ctctactaca | agcacatcat | cacggctgat | 1140 |
| gatgtgtctc | ggagttcttt | ggtggcatgt | acagaggtcc | agcttccaat | taaagacgtg | 1200 |
| cctgacgcta | taaacccatt | tacctttgta | actgcagata | tcatcattcg | agtagactta | 1260 |
| actgatgaat | gtgcagattg | caactatcgc | catggagggc | agtgcaaact | tgacagcaca | 1320 |
| gagaaatttt | gttgtgccaa | tggtttaggt | attggaatcc | caagcatgtt | ggcaattggg | 1380 |
| ttgctgtttc | tctttctaca | atacaaacga | aaatatggta | cctcaggcgg | acaattggag | 1440 |
| tcaagagatt | cttattctga | ttcctcctca | aatcctcatg | gagaaagtag | tagcgagtac | 1500 |
| tttggagttc | cactcttctt | gtacgagcag | cttaaagaag | cgacgaacaa | tttcgatcac | 1560 |
| accaaagaac | ttggagacgg | aggcttcggt | actgtctact | atgggaaact | cccagatgga | 1620 |
| cgtgaagttg | ccgtgaagcg | cttatacgag | cacaactgga | agcgagtaga | acagttcata | 1680 |
| aacgaagtta | agatcctcac | acgtttgcgt | cacaaaaatc | ttgtgtcact | ctacggctgc | 1740 |
| acttcacggc | acagccgtga | actcctactt | gtgtatgaat | acatttcaaa | cggcactgta | 1800 |
| gcgtgtcatc | tccatggtgg | attagcgaag | cctggctccc | taccatggtc | tacacgaatg | 1860 |
| aaaattgccg | tagagactgc | tagtgcattg | gcttatctcc | acgcctctga | catcattcac | 1920 |
| cgtgacgtga | aaacaaacaa | tattctcctc | gacaacaact | tttgtgttaa | ggtagcagat | 1980 |
| tttggacttt | caagagacgt | ccccaacgat | gtcacacatg | tctccacagc | tccacaaggg | 2040 |
| tccccaggtt | accttgaccc | tgaatattac | aattgctatc | agcttactag | taagagtgat | 2100 |

-continued

```
gtgtatagtt tgggggttgt gcttattgag ctaatatcat ccaagcccgc tgttgatatg    2160
aacaggagca gggatgagat taacttgtca aatctagccg taaggaagat tcaagaaagt    2220
gcagttagtg agttggttga tccttctctt ggttttgatt cagattgtag ggttatgggg    2280
atgatagttt cagtggcagg gttggctttt cagtgtttgc aaagggaaaa ggacttgaga    2340
ccttctatgt atgaagtgtt acatgaactg aggagaattg agagtgggaa ggatgaggga    2400
aaggttcgag atgagggtga tgttgatggt gttgcagttt cacatagttg tgcacattca    2460
ccaccaccag cctcacctga gtgggaagaa gttggattgt tgaagaatat aaagcctact    2520
tccccaaaca ctgtcactga taaatgggaa agtaaatgta ctacgcctaa tatcagtggt    2580
taa                                                                  2583
```

<210> SEQ ID NO 10
<211> LENGTH: 860
<212> TYPE: PRT
<213> ORGANISM: Glycine max

<400> SEQUENCE: 10

```
Met Val Phe Gln Ser Leu Ile Cys Leu Tyr Pro Ile His His Ser Pro
1               5                  10                  15

Asn Ile Tyr Glu Asn Gln Thr Leu Arg Val Ser Asn Thr Ala Phe Ser
            20                  25                  30

Val Ser Arg Pro Asn Thr Thr Asn Ser Lys Gly Cys Leu Pro Leu Pro
        35                  40                  45

Leu Thr Gln Asn Leu Thr Leu Pro Ser Thr Arg Glu Phe Asp Ile Ala
    50                  55                  60

Pro Asn Gln Thr Asp Ile Arg Leu Phe Tyr Gly Cys Gly Ser Leu Pro
65                  70                  75                  80

Trp Leu Glu Glu His Lys Val Gly Cys Phe Asn Glu Thr Ser Ser Val
                85                  90                  95

Leu Ala Leu Tyr Lys Glu Asp Lys Asn Ile Ser Phe Val Ser Lys Asn
            100                 105                 110

Cys Gln Gly Glu Val Val Asp Thr Ile Val Glu Asp Gly Ile Ile Gly
        115                 120                 125

Gly Asn Glu Glu Ala Leu Thr Lys Gly Phe Leu Leu Thr Trp Lys Ala
    130                 135                 140

Gly Asn Cys Ser Val Cys His Asn Thr Gly Gly Arg Cys Phe Cys Thr
145                 150                 155                 160

Asp Arg Val His Ser Ala Lys Cys Gly Pro Asp Asp Pro Glu Val
                165                 170                 175

Val Phe Arg Gln Thr Phe Ser Phe Thr Ser Ser His Arg Asp Arg Glu
            180                 185                 190

Ser Thr Arg Lys Leu Arg Asn Glu Ala Gln Lys Phe Glu Ala Thr Asp
        195                 200                 205

Tyr Asp Thr Glu Arg Val Phe Tyr Leu Ala Ser Leu Thr Gly His Val
    210                 215                 220

Glu Val Lys Cys Glu Pro Asn Arg Leu Lys Arg His His Ser Leu
225                 230                 235                 240

Thr Leu Ser Asn Cys Leu Ile Ile Ser His Thr Leu Ser Thr Ser Phe
                245                 250                 255

Glu Arg Pro Asp Cys Gly Phe Leu Pro Ile Arg Asn Cys Glu Asp Pro
            260                 265                 270

Leu Lys Phe Lys Met Ile Gln Leu Gln Asn Asn Gly Glu Trp Phe Arg
        275                 280                 285
```

```
Val Val Leu Val Ala Gln Leu Arg Asn Ser Ser Ile Ile Thr Phe Gln
    290                 295                 300

Ile Arg Asp Lys His Leu Tyr Asp Leu Leu Gln Asn Glu Ser Cys Glu
305                 310                 315                 320

Ala Phe Arg Tyr Asn Tyr Thr Ile Pro Pro Phe Phe His Phe Ala Ala
                325                 330                 335

Leu Arg Ile Gln Tyr His Thr Thr Leu Phe Arg Cys Asn Arg Ser Leu
            340                 345                 350

His Val Ser Pro Pro Thr Gly Met Leu Asn Tyr Thr Lys Cys Pro Asp
        355                 360                 365

Tyr Asp Leu Tyr Tyr Lys His Ile Ile Thr Ala Asp Asp Val Ser Arg
    370                 375                 380

Ser Ser Leu Val Ala Cys Thr Glu Val Gln Leu Pro Ile Lys Asp Val
385                 390                 395                 400

Pro Asp Ala Ile Asn Pro Phe Thr Phe Val Thr Ala Asp Ile Ile Ile
                405                 410                 415

Arg Val Asp Leu Thr Asp Glu Cys Ala Asp Cys Asn Tyr Arg His Gly
            420                 425                 430

Gly Gln Cys Lys Leu Asp Ser Thr Glu Lys Phe Cys Cys Ala Asn Gly
        435                 440                 445

Leu Gly Ile Gly Ile Pro Ser Met Leu Ala Ile Gly Leu Leu Phe Leu
    450                 455                 460

Phe Leu Gln Tyr Lys Arg Lys Tyr Gly Thr Ser Gly Gly Gln Leu Glu
465                 470                 475                 480

Ser Arg Asp Ser Tyr Ser Asp Ser Ser Ser Asn Pro His Gly Glu Ser
                485                 490                 495

Ser Ser Glu Tyr Phe Gly Val Pro Leu Phe Leu Tyr Gln Leu Lys
            500                 505                 510

Glu Ala Thr Asn Asn Phe Asp His Thr Lys Glu Leu Gly Asp Gly Gly
        515                 520                 525

Phe Gly Thr Val Tyr Tyr Gly Lys Leu Pro Asp Gly Arg Glu Val Ala
    530                 535                 540

Val Lys Arg Leu Tyr Glu His Asn Trp Lys Arg Val Glu Gln Phe Ile
545                 550                 555                 560

Asn Glu Val Lys Ile Leu Thr Arg Leu Arg His Lys Asn Leu Val Ser
                565                 570                 575

Leu Tyr Gly Cys Thr Ser Arg His Ser Arg Glu Leu Leu Leu Val Tyr
            580                 585                 590

Glu Tyr Ile Ser Asn Gly Thr Val Ala Cys His Leu His Gly Gly Leu
        595                 600                 605

Ala Lys Pro Gly Ser Leu Pro Trp Ser Thr Arg Met Lys Ile Ala Val
    610                 615                 620

Glu Thr Ala Ser Ala Leu Ala Tyr Leu His Ala Ser Asp Ile Ile His
625                 630                 635                 640

Arg Asp Val Lys Thr Asn Asn Ile Leu Leu Asp Asn Asn Phe Cys Val
                645                 650                 655

Lys Val Ala Asp Phe Gly Leu Ser Arg Asp Val Pro Asn Asp Val Thr
            660                 665                 670

His Val Ser Thr Ala Pro Gln Gly Ser Pro Gly Tyr Leu Asp Pro Glu
        675                 680                 685

Tyr Tyr Asn Cys Tyr Gln Leu Thr Ser Lys Ser Asp Val Tyr Ser Phe
    690                 695                 700
```

```
Gly Val Val Leu Ile Glu Leu Ile Ser Ser Lys Pro Ala Val Asp Met
705                 710                 715                 720

Asn Arg Ser Arg Asp Glu Ile Asn Leu Ser Asn Leu Ala Val Arg Lys
            725                 730                 735

Ile Gln Glu Ser Ala Val Ser Glu Leu Val Asp Pro Ser Leu Gly Phe
                740                 745                 750

Asp Ser Asp Cys Arg Val Met Gly Met Ile Val Ser Val Ala Gly Leu
            755                 760                 765

Ala Phe Gln Cys Leu Gln Arg Glu Lys Asp Leu Arg Pro Ser Met Tyr
    770                 775                 780

Glu Val Leu His Glu Leu Arg Arg Ile Glu Ser Gly Lys Asp Glu Gly
785                 790                 795                 800

Lys Val Arg Asp Glu Gly Asp Val Asp Gly Val Ala Val Ser His Ser
            805                 810                 815

Cys Ala His Ser Pro Pro Ala Ser Pro Glu Trp Glu Glu Val Gly
                820                 825                 830

Leu Leu Lys Asn Ile Lys Pro Thr Ser Pro Asn Thr Val Thr Asp Lys
    835                 840                 845

Trp Glu Ser Lys Cys Thr Thr Pro Asn Ile Ser Gly
    850                 855                 860

<210> SEQ ID NO 11
<211> LENGTH: 56668
<212> TYPE: DNA
<213> ORGANISM: Glycine max

<400> SEQUENCE: 11
agaaccaccg tagttgttgt cttgggaggc tttcttggag ttcttgggca cttcatctgc      60
acagaagaag atgatagttg caataagaga gagggtcaca cataacacaa aaacaagagt     120
tccaattcca agctcttctt caccactctt cactactccc atctctttca attgcctcgc     180
catcttgtgg tttctaagct tctgatctct gccaaagata aagagaaggt gttagctaca     240
aatggttact gtcctttgcg ccacgaaaag gtgacgtgga acaatgtcat gctacaagga     300
aaataaaaaa gaacatgtga atttgaatgg ttctaagact ttcataatt ataattatcc      360 tcacttttc ttcctttta gttctacttt tttttctatt ctctctttag attttctct        420 tcctttacct ctatacatcc atatataata aatataatta atctacaatt ctagagtact     480
aattaacatt ttctctaaaa taattaaggt ggattgaagt agaaaatga gagataaaaa      540 taaaagaaa atagaaaata agtgatatcg agaaaaaata aaacaaaaaa ttgaagtcaa      600
aataagatgg gaaaaaaata tataagtaga tgactataat tcttcaaaac tttacgcagt     660
tgaccgatta acttaatatt gattccttcg ctttttttagg acggcgaatt aaaaaaatat    720
tcgtgtgcca attatgtgca catttagttg gcagccacac aagtctgaat tgttaatgaa     780
cttagtccta atcttatcct taaagtggca aattaggatg tgaatccgag agaatttaat    840
ccttgcgttg cagctaaaat ttgacacgac ttaactaaaa ttttctcgct cgttcatttt    900
ctttactttt tctatattaa ataattttag tattaagaaa tttgctatat ttttaatttc    960
tgaaacaagt gttattactt ttcaattctt tcttaataaa atttctgtat agtatactgt   1020
ttttcttcct atatactact ttcattacca tgtataatgt cattccaact aattcacata   1080 taattttta cagttaaaat ttgataaaa taaatatttt ttaatatcta aattatattt    1140
tgaatttacg ataaataatt tatattatga taaaaaagtt gattaataaa aactaaaaca   1200
gacaagtgat taagaaaact aaatatatga acaaagacaa tgagagtggg tcgataaaga   1260
```

```
aatatattag gttagttatt aaattaaatt aaaattgaga tatatatgaa atgaataaat      1320
aaaatataaa tgcttaatat ataggattct gataagacat ataattcaac gggaatgata      1380
gtaattctta aaatgttcat ttgaggataa gtcctgaaaa taatctaaat attgaagttt      1440
gaaaaagtta taattttgaa gtggattaaa tttcaatagc ttttctacaa aaatatcaaa      1500
gttaaaaata attacatcac tatttaaatt atttattata aatctaaaat ataatttata      1560
tatcaaagat tcataaatta tacatgtaat gtgattcata tatttaaaag tatttattta      1620
ttattaattt taattatata acataaatat ttattttata aaatgtgaaa gcgaaaatac      1680
tagcatcaaa tattaatctc ataaaaagtt actaaagtaa tttagcttaa ttatttaaaa      1740
aaatgtaaaa attattataa acttttaat aatgaattca attcttaaga ataaaaaaat       1800
aaaataaaaa tctcataaca agcttatggt tctacttgaa ccaatgcaaa aggtgatggt      1860
gtttggtgtt tcataaccaa cctattccga tagtctttgc ctcgggatcc atcttttcat      1920
agatagtgat ccctacccta tcctacctac caatcaatac atggatcgtt tacaacttca      1980
ggtgagtata ttagctgtag ttacggtaat ttgcggccca ataacgctta aaggattttt      2040 tttttttctga agttaaacga gtttaatcta catgcaaatt catttattta tataaaaaaa     2100 taaaaatat acattttaaa aaaatgtaaa ttaaaaaaat aaagatattc tgagctagct       2160
ggtgaattat tttggccaaa ctatagtaaa agatttata aacgaggata aaaaagtttg       2220
caaaccaatc catgagttgg cctatttaac tgaaagctta aatgaaacat tgggcaattt      2280
aaatttaggc ctacataaat tggtccattt aagtattatt ttggtttgag accaccgata      2340
tctcgtaata gaggcaatca ttcttaagta aagcagaact actgttgtaa ctaattgagt      2400
catcatggca gctacttagc tatggtaggc ctagggccta tatctctgtt acaaaaaaaa      2460
tgacacaaac gatgaattag tagtttagcc aacccgaaat ttaataacca tacataatta     2520
gaataaaaat taatgttttt ttactataag actcctgcat taaaatctgt atagtttcgt      2580
aaccgacatc ttcgtaacta actaacccaa caataattaa ttgcattgaa agtgaactac      2640
catctgagac ccaataataa ttatttacat taaaagtgaa ttgcacaatc tgtgagcaat      2700
ctattgacac aaaactgaga caaaacttct ctgcaacatt aggactataa attcagaaat      2760
gaccacctcg gtaaaacatt tatatgacca caagtccaca gctttcggcc cccaattaat      2820
tgtacgagca attgttgcta aagaaagaaa agaaccactc actgaaattt gtgcacatat      2880
gaagaaaact gaccaaaaaa agctgcagca gaattcatga gcctcgtcaa tgccaacaag      2940
agatgttact tgatacagta cattcactga ttcacaatcc tagcattcat tcattcccaa      3000
tcaaaaatca ctttatcata catcaaaatg gcccaaacca atagtcaaga aaagaaacaa      3060
taaatacagt accccatgta attcatctac tttcaaaaca accttattgat agttgcaaca    3120 tagttgggat atcaataaat gaaggcaagt cagccagaaa ataaaataga tcacgaaatc     3180
taacacaaga tagatatccc agtatagtat agaaaaatag tactacattg tagccaaatt     3240
gtgtgtgtgt gtgtttgcac tctacacatt aaaaagaacc ttaatgagaa gctggttgca     3300
aagaagttct agtagagtgc tcagaagcat tggcaaggcc ttgcaacatt ctcaaaatct     3360
cacttgtgtc ttccaaataa tactttgcct tgctaggttt ctggccaaca gtgcatggaa     3420
acacttcagc aactggagat agggttgcct ttgcattcat gattacccca aacatgtcct     3480
cgtctgatct gtcatctcca atgcatagaa caaaatctgg aaacactccc ttttgttgca     3540
ttgttaagag aagacgttct gctacaatac ccttactcac accctgcacc aaaagttgaa     3600
```

```
caacaagagg agataatcaa cccaaccaca tttcatgacc aaatattaga attaattcct    3660
gtgatctaca caagttcttt agaaggaatc caatcccaaa tgcactccaa ttgttttgaa    3720
cagaatatta tggaacaaac agcagtcaac tatgcaaaca tagaacataa cagggttgtc    3780
aaaacatggt tctgggccag ttatgagcac cactacaatt aaatcacctt gaaggtccaa    3840
atccaaagat cctttctgat aaagaggcc acacaagtca aactataag atgtatataa      3900
aatataaact tcttcaatta taaatatgtg taacctaaaa atgactaaaa gtggaatttt    3960
tttttttact gacctgaggt ttcacttcaa caatgtttgg actacttta acagaaacag     4020
gctcattggc aagaacactt tccagatgat caaaagctc cttagcttgg catgaaccaa     4080
agtctcggtc tgcatactcg taattccaaa ctagagcact ttctttggcc tctatgtttg    4140
aaccatcagt tgtttccata tataactgca taaccggctc agcaatctgt ttccactcaa    4200
aatcaggtac tggaatacaa gtatcccatt ctgcatttcg atttgtcctg ataaaaaaa     4260
gataaagttc agtttaagta cataagctag ctctgccaag gaaagtact tttcctcaac     4320
attctctcat acataaattg aaacagtgag tttatttgc tgttaatgat gaaaaaaatc     4380
caatatgatc cctcaatcca atcaaatttt ggacaaaaag aatcaaattg catcattctt    4440
aaaattaaca aaataaacaa gtaaaaagaa ccattaatat gatttgcagt aaccacaaac    4500
tcttcctgct cctaacacac acaaggaaag aggatatacc tcacaaaata accatgctct    4560
gcagcgattc ccatcctttc acaagaagaa accattcag taagagtctt tctctcccctt    4620
ccacttacaa tgaaaacaca attcttggtg tccctgcaca agatgttcaa gatgctaacg    4680
gcttcagcat taggtgttaa actcatcgac ccaggctgca ccatagtgcc atcataatcc    4740
aaaagaattg ctcggtgctt ggtcctctta taagctgaaa caatatgttc cacagatagc    4800
tttctaaagt ttggatccaa agcaatcact cggaagccta aaccaaaacc aattccccag    4860
catctcctcc tcagatgatc tctacatgcc cttccagat cctgcaagaa gctacgtgcc     4920
caatacgcaa catcatgtgt actaacatac ctataatgct tctcatgccg catctgcttt    4980
tcagcctctg ggaccatcaa cgcagaatcc atagcttcag cgacagaatc aatgttccat    5040
ggattcactc gaattgcccc acttaacgaa ggggagcagc caataaactc agacaccacc    5100
agcatactct tcttttgagt aagcaggtct gtccctaaaa tctcatctat cttctcattt    5160
ccttgtctac aaatgatata ttcatagggt ataaggttca tcccatctct cactgctgta    5220
acaaggcaac attctgcaat cacataataa gcaattcgct cataactctg aagtggtgta    5280
tcaatcaaga ctacaggtgt gtatccaggc cttccaaatg cattatttat cctcttcatc    5340
gtggcataag tttcactttg tacctcctgc acatcctttc cacggcctct tgcagggtta    5400
gcaatttgga ccagaacaac tctgcccctc ttatcaggat gttgtaaaag caattgttcc    5460
atggccaaaa gttttaagct gattcctttg aagatatcca tgtcatccac cccgagcagc    5520
acagtttgat ctctgaactg ttttttttaac tctgcaacct tgctttctgt tcgggatga    5580
ctcatgacag attggagctg acctatatga ataccaacag gaagaatctt aatgcttact    5640
gttcttccat agtactcaag gccaatgtag ccacgcttgg attggtaaga atcccaagc     5700
attctgctgc aacaggagag gaaatgcctg catatcaa agtatgaaa cccaataagg      5760
tcagaattca gaagagctct aagaagttca tccctaacag gaagggttcg gtatatctca    5820
gacgaaggaa atggactatg gaggaagaat cctagcctca ccctgttaaa tctctttctc    5880
aaaaatgtag gaagtaccat cagatggtag tcatgaccc acacaaagtc atcatcaggg    5940
ctgatgactt ccatcacttt atccgcaaat atcttgttca cagaaaggta agcttgccaa    6000
```

```
agggacctat cgaatcgacc accaagatca ggtgacaggg gaagcatgta gtgaaacaaa    6060
ggccatagat gttgtttgca gaatccatga tagaatttac taaaaagctc aggagggagg    6120
aacgttggca cacatttgaa agtgtcaagc aagtacagag caacatcatc ttgctcactt    6180
ggctcaatct cttctttaag acaaccaata tagatagttt ccacatcatc cccaagacca    6240
tctttcagct gtaaaagaag tgagtcctca tcccatgtga actcccaagt accgttgtct    6300
tttctgtgtg cctttaatgg aagctggtta ccaacaatga tcatcctctc ttgagagact    6360
gaggatggag tatcagagca aacactgttg ctggtttcat catctaattc agacagtact    6420
ccagcaacag ttgccactcg agggagcctt ttcttctcac gactgaaagt cggggagcca    6480
caagaagtaa gatctaacaa gttagaatat gaccttgaaa ccatttttgat gatggccaaa    6540 tgataagctt tggtggacaa gatgcagaag caggcttcta ttaattgttc acttcacagt    6600
ccttcaaaca accataataa ggatgaaatt tcagaaatct gaaaacaaa ttaaatgcca    6660 tttatagcac gaaactaata agtccagcag aatcaataaa acctaatgtt acattacaag    6720
aaaggtccat aacaaaagtt tggtatgttt tctttacacc taaggattta aaaaaattca    6780
ggtttggcac atagtactca tgagaaaaga gcagagaggg agataaatct aaaatctcac    6840
actagaaccc cttcagctgg gattgacagt agtagtatac tttaatgaca aattatattt    6900
cgaagaatac cacgttgaac aaaaaaggta accataataa caatttgaga aaatcctaaa    6960
tagacaacat ttgaatctat gaatagaatt attaataata ccacctacca aaaagaaaaa    7020
ttcatccact aacactgaga attgaagcaa cgttgaggat ggctgcgtga acacttaaat    7080
ggatccaaac accaagatat ataaaaaatg caagattagc ccaccttcct ttgatgaacg    7140
aagaagctca agagaggcca aactagccca aaagatgaat gaacgaatga acagaagagc    7200
aagaaaggaa gaaactttttc tcaacagcaa tgaagaaaaa tcctaaccct tgaaaacaac    7260
aagcaaaaga gaggtgtgag ttgtgatatg agagacagac agcaaaagat tcttcttttc    7320
tttctcttct cagtcacaca cacaaacact tcacctgagt gagcaatggt gtcaactggg    7380
aatccctttt tctcttactt ttgttacaaa aacagaaaat tcatagtgat attttttgcc    7440
tattacaccc aactaacgac aaattgggat gtctttatac aaagaacttg attctctcct    7500
cccctcaaat ctcactatgc ctatgtctct atctcagtga tgtgtgatga catgactacc    7560
ccaaaacagt gaactccaac atccttaacc acgttagtt ttttcttaat gaaagattaa    7620
ctccacctaa ccctcctcaa atgtgacggt ggtgcttcac tgccaccact aagacatgct    7680
taatgcacac tagagcgcgt gtaagcacat caccattcat tttttttcca gttccagcat    7740
atattccctt gtcactctct tgtgtacaaa gtgggcttgt ctggtttttt taggttcaaa    7800
tattattcta actgactcgt gaattaatt taacgcaaag tagtgtttaa gtttcttaaa    7860
ttgtgatttg acatggttaa atgcctgctt gaacagaatt aatttatta tgatttctgg    7920 tcagagtcac ataggaataa ctcattaatt cttttgtgca tattgtttcg aaaatatttg    7980
aacaatttca ttttaaaatt taactttagt aaattttcta acaacattcc taataagagt    8040
tgtttataga aatcttacaa ttaagaacta actcttgtat aattttacca atggagaaat    8100
tcgcgtggta attcttaaaa agaaaatcta attttaactt tttaacaatt tatttttaga    8160
aagaaattaa ttgaaattct caaattttat atagtattgt aaggcttata tatatata     8220 tatatataca acaactctac cataataata ttggagattc tcttgaacaa tgtactaatt    8280
atgctgtatt aaaattaaat gttagtttta ttttgtagaa attattgaca agcacgacct    8340
```

```
tagaatttgc tgcagagtat attacacgcg caatgttagt gaacaacatt gcaacatgtg    8400
tctttgttaa aaaaaaagt gtcaatggat agagattatt ttatgaacaa agtgattctt     8460
aattgttgtt ccgggtcacg acatatttgg ctgattttt tttttaaaa aaaaaagag       8520 actgtagaaa atattgctc tttcaaaaca ggctaatcca aatatgcatt caaatcttaa     8580
gcattatcat gcaaatattt ggaagaagag aatataagag aggggtaaat tatgtaaaaa    8640
cgtacgttat aatagaatac aacagatttt tttgacaggt agaatacaac aattacataa    8700
atgacataaa tgttactacc attatcatgt acataagtgt gatgcaacat atatatcaat    8760
ttatgttttt gaacatttta ttataaaaat tacgtaaaat aaatatagtt tatggtaaat    8820
attaatttaa attttgtta atgtttagac tatttaagtt attttcacca aaaatataaa     8880
atctaatctg aaatctgtta taaaaaatt attgcttact tatgatattt aatgtttaaa     8940
ataattgtaa aatactcact ttaaaacatt tatatatata tatatatata tatatatata    9000
tatatatata tatatatata tatatatatg ttttaaatta acatctttga aaaaggggt     9060 ggttcttcc ttcatttcac aggtttattt ttacacaacg aggacgtgct tctttaaaaa     9120
aaaaaattat ggcgtcattg agcattggaa acccatttta gattttctat cattatatca    9180
ttttgtaacc cttctctttt actctttgtg ccgtgcacga gcctttttta tttgacttcc    9240
ttttcagtca tggagcctca agctaaaaat tattattatt attatttat cgtagttgct     9300 tatttgctgt tcgcggtgga gaataagaaa ttgtgacaga gacgtttagt tttaatgaat    9360 gtaaattt aagaaactaa gctaaaaatt atcaaaattt agttcaatca ataaatttta      9420
ttccaacatc tcaatcaaat tccctttgtt tgaatgacat gtattttttt tagaccccta    9480 attttaata atatatggtc attaattttt tttccaaaag aatataaata ttagttaaaa     9540
agacctcacc tcaaaccac tttagagcta aaaatatatt aaactaaccc tattctttgg     9600
tttgagccca tcatattgaa aacttcagaa ttcaatactt ataacgaatt agaatagatc    9660
aattatttta tagaaccaaa tcaatctaag actttgaatc tgactcgtta acatccttaa    9720
tttatatatt tctttttt cctatttagc ttttaatcca aattgtaatt attcaaaggt      9780
atgattgtaa ttttttccttg atgtgttgaa ctttatctgt ccgtacattt cattattttt   9840
tgtcactctt gatcgtgtgt taaaatgaag tgaatacatg caaaagacaa tttgatactt    9900
aagacaagac aaatatcatt tcaatacagt aaaaagaaaa taataaatga aaatgaataa    9960
ttattttacc tcgaaagtcg cactctttgt atatacgcat gtatagactt taggattcat    10020
gggtcatatt gttaatgtga tgttaatcct ttattatatg gtaatattat cttaattcaa    10080
ggattatgcc tctaacattg acattgtcaa ctgtaataag atcgaacaat cctctcatga    10140
gtattgttgg attatatgat tatctaaggg ttctagatcc aagtgggata aaaaacaaaa    10200
acattacttc tcatacaaat cttactaaca ttaattaaac aaggcattaa atatatttaa    10260
tttcttaaaa atataaaacg ttttaatat ttactttatt tagtactact attaattagg     10320
agaattcgta ggaagagtaa gcaggagaat ataaaattat taaagaaaac actagtataa    10380
tttatctgga tgtgtctcat gatcacacga ccgacgttat ttttagccat acagcaaggg    10440
tatctccaag aacataagtt gttatatttt tcttggcttt tgccgcgaca tcctttatat    10500
ttaaagtgca tcccaaactt ttattactag aaaattactt gtcatatgat ttataaattg    10560
gttccatggc aacttcaatc gatatctgga ccgaacatgt tagtttagaa ttcgtaacgt    10620
ataacaaaat agattgcgtg atccaatgac ttcaaaaata tcaccattat caattactcc    10680
aaaccaagtt caggttacta catatcatct caaataaaca ccacgcttga ggtcgccaat    10740
```

```
catgcaacgt agaatttaat taatggccag ctttattaat attaatcaaa tgttttcttt    10800
ttgctgaata ataatattaa tcaaatgttt taccacaagt aaaagtaaaa gcaaaaaaat    10860
cattatttaa tattaattat ttttaaaaa ataaaacaaa tcctgagaat acttttttat     10920
ttagacgtcc aatatatttt caagaaaaac aattttaag aaagtaagta ttgtaagttt     10980
aattgcattt tcggtataac atttacacca acaataaata ataaatattt ttttattggt    11040
gctgtttaag ttttaaattt taataacctt atttttggac cagcttcgat aaccgtaact    11100
ttcccttaac atttaacagt cattaaattt acttatttaa ttattgctat tacatcaatt    11160
atcatttttc tttctttctt tcttctttat actccaatag gtagacctag aagtttatta   11220
gaagtccaag ataaaagcaa gggacaaata gtgaaatagg agagaacctt ctaagttata    11280
agtagagttg tgttggtaac atcaatgatt tgcttgccac ttttatataa taaggctatc    11340
attattctca tttgtgttaa gttgcttctt gacgttgagt gattgtgtcc acctagcctt    11400
gataccattt gtaatatttc aatcatcacg gcttaaccaa aaaaaaaat tgaagaaaat     11460 taatacaatc attactgatg cgaaacttgc tactcgatgt ccattcctca tgcgtcataa    11520
ttagccttct ttttctcag ttacaactta acaataatta ttaactactt ttccttttc      11580 cttagttatc ttttactttc ctaaaaaaaa aaaaccaaaa cttttaggct ggcaaagtca    11640
gaggaatgac aaagtctcaa acttatagca aattaacttt ataaaaaagt taacgggctg    11700
atgagaagat ttaccgaaac attatagaac aaattgttga atactaataa ttcaaaatat    11760
tcatttatta atggggtatt taaaaactat caaatgatta attttattcg tttgtttatt    11820
ataaaacata tgttaattaa gtatcaaatt gtgtaaattt atacattaaa taattattta    11880
aaaaatagac tacattatac ttttggcctc tatataatat ccaattgtag tttttggtct    11940
tcttttttta attcggcaat tttaacgggg acggaaccaa aagtgtgtta aagggagacc    12000
aatttttttt tacataatta tttaaatatt taatttctaa taaataatta tttaataata    12060
ataagtttta aaaatatttt tttattgatt ttatttataa aattaaagat agggtctatt    12120
actataaaaa aaatttaaac aaatatcaac ttaaaaactt attttctta tattttttt      12180 cattaatatt tttattttt attttatttt tttctttata tacacaaagg gttctaattt     12240
tgtaaaaaaa aatcatgtta gacttttca tgtttttaa aattagtcta ctatttagta      12300
aatatttgtt tgttaatagt taaaattgta acattaatta ttacataaca ttaaatagat    12360
ggcgtgtaaa agtgtttaga catgtggata ttttgtttt tatttttat ttagtaattt      12420 ggaggtataa gggatttttt aatttgacat ccaattttt ttttcaaccg gattgatcta     12480
ttttataggt aaagtgatac ctttcatact cagaccagga taatcaaacc tagactttga    12540
ttaattatta tattatttta gggtaaagtg tggataatct cgttgacgta tgcgttattt    12600
tttccatgca acgagttcaa tgggaaagga ataaattaat agagggcaat gaacaagtta    12660
aattttcttg agtaatgagt acatatatat agaaaccata ctcaagagtc aagactaatt    12720
tacactcagg ttgccttcag ttcgtggcgt catggtatga aaaatcgtcg ttagccacga    12780
tgatgatggc tctaaagtg tgttgaatgt ctattttcag tttgcaaggt aaaaaagatc     12840
aaaatttcta acaacctttt gatacaacgt agaagcaaca aatggttgct gcaactcaaa    12900
ccttgaatgg tttgaaaggg aggtgaattg gaatttttt ttttttgttac aggtgaattg    12960 gaaatttgca aaataataaa ttatatctcc aaaaatgctt tctctcataa gattttttgc    13020
taacgtgggt ttatctagtc taatgtcaac ccaaacacac aaaatggtgt cctgtaatta    13080
```

```
aaaaaaaaaa actaaaaaac tagatttagc attttattac catcagttgg gttgaatgtg     13140
tttttctcat gaaaggttaa taggcggcgc acgcacatcc acattttaat tatattttt      13200 agtttgtatg gaaaacttta aataatatat caaaatagtg ttatagtttt tatagtttta     13260
aaaattctga ttttattaat taattttaa gttttctttc atgttaattg ttttaaaaca      13320
tcatatttct aaaacaaaaa atgcaataat tttatgttgg aatcttttgt ttttaaatct     13380
caactattta ttttctcaac attttaatat ttccaaattt agtcttttcc tctcaaattt     13440
aatcttctta tattttttg ttcttgttat gtatgtaaag actgtgtata aatttctcat      13500
aattgaaata tttttccatt aagtattttt tgtgtactat aatgcataag acacctatta     13560
attgctttca aaatgaaata cccattaatt agtttctaaa atccatgagt ttctatttct     13620
ttgaatggtt tggaatccat ctctaatcat atacgttaag atttgttcat aaaaaaattc     13680
tttgaattag tttcataatc ttcaccaaaa aaaatttgtt cgtaatcttg agcaaggtga     13740
catttaggat ataccttatt tcttggtaag ttatgtacat ctcataaatc ttataagtta     13800
tatgtttttt ttcttttaa atgctattat ttaaatttaa ctaattttaa ttttaaattt      13860
tagcataacc atatcaaaat tagtagctat aaaaaatgtt agcttaaata atcatttagt     13920
cccaataaaa tattcaatt tttatttag tcctttaaat atattttttg ttgttagtcc       13980
cagtgatttt cttaaatttt aaatcttttg ttgttagtca atgttgcagc aacaacgtaa     14040
cgttattaac agataacgta atagaaatat atggagttta ttgatttatt aagccattaa     14100
agagagtctg atggaataaa tatgtgtaat tttttgtaa tttgttttta aattctctta      14160
tatttacaat aattgataaa tgattaaaaa tacagtttat aaaaaaaata tgtagttatt     14220
caattagact ttttaagaat ataacgagtc aatatcgtca attaatatta ttatttaaca    14280
aaaaattcaa ttttgtaggg aaaaaaatct ttgaaagact aaaactaaaa atagaatatt     14340
ttataagcat caaattgtta tttaagctaa aaatgtatct taattcaatt actttaaatt     14400
cataattttc ccttaaattc aaaagtcttg tatcattttta attcataata ttgttaacaa    14460
ataatattgt tataaaaata tttttatttta aattttatta aaattggaaa actcatataa    14520
tacacgaaag acttgttgat acatttgcta aaagtaaaat gctcaggata caaaaggaca    14580
tactcaaaat atgaaatttc cgtaaaagaa ttgctaatat aactaaataa ttttcaacga    14640
ataattaact gaacataatg ttatatcttt ggtgttaatt atcggtacaa atttatataa    14700
tcagagatgg atatttcgtc atattccaaa gactgaggaa tattcttctt cttatttttt    14760
tttccgagag tcaaaaccaa gattattgac ttgtgaccaa agaatactaa tgaaagagac    14820
gagctaactc cccaaaatga tgggttgata taatttagat ctatggtcaa atcacactta    14880
ctttgcaaaa ccaaaattat gagctaactc cccaatttaa tttatctttt atactccaca    14940
tatggttttt cgtctaaaga tgatttgtcc atcattaaaa tttagaatat tatcaatttg    15000
ttgcttaagt ttttatatac aattttaata gttgaatgca ttcacgttca cggtataaac    15060
taattattgt tatttaatta taaattatta ttggtttaat ttttaagata attttataaa    15120
agttaattga tttattatat atggtaattt gtaatgaaat aacagtataa catgcataac    15180 ttttttctc taattttaat aattgtcata aaaaaggtaa aatatatttg gagttgctat      15240
ataatttaaa aaatatcaat tttgttcaca taaattttta gtattaattt ggttttata     15300 aaaataaaac atatttttat tatttctcag tcataatttt gttaaatgat aatttaattt    15360
aatgtaacta ataaatttat acgtataatt tgattataac taaactaaat aatttatgac    15420
agttaaaatt ttaaaataaa ttaaataatt ttttatactt aaaaactttc aaaaattgta    15480
```

```
attttttttgt cagttcttaa acgattttct tacactttcc ggtaagatta agggaagaga    15540
tgaaacataa taaattttaa tatcttctaa atatgctcag aaaagataga aaaaaaaagt    15600
aaataaattt attagtcatg taagtcaatg atctaacgga gttataactc aaaattaata    15660
aaaaatacgt tttattttcg catgagcaaa gtaatataaa aatgtgtacg aaaataaaat    15720
tcccactttt taattttata aagattctaa acatatttta tgctaaaaaa atattgtcat    15780
tcttttacag aagtcgctgc ctgtaagaaa aaaaaaagtt tgtggctttg atacgacctt    15840
aatgagaatc aatctaagtg ttgaaagagt tatttagtgt tgtaattcta tcacctgtgc    15900
atgtcgagta ttcaacggtg gaagaagtta catgtatcaa ttcctagttg aaaatgttat    15960
gatttgaatg accgtaacta tgcttaaagt tggggtttac gtggcttaat ttgttcccct    16020
atagaaaaag acatctaact gtctacaaat aataaagagt tgaagtgggg aacccaaccc    16080
caccaattat tgttacaaaa tgattctcct tcagctaccg aaaatgaaat agtggttata    16140
attgtcatca aaaactagtg taaaaatata atgatatga aatagtgtg gtttttaagg    16200 gagtgtctag attagattag tggtgattta tgaaccgatc ttctttattg gagttaggct    16260
gttggagatt agctcgcgtg agttaagttt ataaaaaaaa tatagttgga tggcctttgg    16320
aagatttgac ctaaatgttg aatgaaccca ctcacacatt cacacatgaa ctctctattc    16380 tttgttttg tatccgagaa acccttagt catttaattt atttttatta gtataaaaat     16440
cttctaactt aaactaaact attgatgtaa atattgcaaa tatatatttt atagtttaca    16500
taatatatta atagtatgat ccagtgacat tgtatattaa ttttatgtac caaataaaaa    16560
ctttcgttca cgtcaaaaaa taaaaaactt ctgttagtgt gacattatgt tattagcata    16620
ataatactaa ttattttatt ttgttggata aaattttaat tttcaatcat gtgaaatgat    16680
atcatataat tcatggaatc agtttgaacc tcacctagtg gaacaaaatt ttattgtttt    16740
tgttacataa aatttacatc aatatagata agtttagtac atggattttt tctttacaat    16800
taaaagaaat aaaaatgtat tgtgcaacaa aaaacgagtg atcattactt atatatttat    16860
aagatgatat tagaatttat tataacaatc tattattggg cctatagttt cacccgttat    16920
tgggccatta ttttttttaac ccaattttta aaactgaggc aacatgagaa attcttttgg   16980
atagaaaaaa tcttataatc caaacctatt gcgtttagat tttatcctaa gtcaaatatt    17040
tttttaaaat acgtttagat tttggacaat tgggtaatct agtatatatt ggttaagtca    17100
aatatatttc gttttctctt taaactgaag attactttaa cctatatata tttcctttat    17160
ggtatatgtt catcaatcct gttttctcttg ttcgaaacct accttcttat tcatgccagt   17220
agacacgtcc tttttaatgt aattttgtga tacgccaatt gaatggattg attgagagat    17280
acgtcacata tcttaacatg tttaagtata acttgggaga tttttagtt aaaagtttaa    17340 acataacctt taataactca gaaacttgtc ccaagaaatt atgaatttta tagttgtaat    17400
atattttaaa tgatatgaac attcaattat tccattaccc taaatatttc atagaaatat    17460
gttgttgcaa gcacttgttt tttcagagaa ataaatttac aagcattatt ttcttttaca    17520
tacttaaatc aggagataga tctaaatcta agtgtagcca attagtggta cagcttatat    17580
tatagtgtac tttatttcgt gcattatatt gcatatctaa acttcatttc ttcttctttt    17640
ctttcacagg tccccttgga atcttggtta gaactttagt atccaatgtg ttgaacaatc    17700
tctgcacgtc ttggtttcct ttgcttgcta gataattcac ctcatattca tatctctcat    17760
acataatggg aagagtcacc aggcagagga acactgtaaa acaaagatat agcagatcaa    17820
```

```
taaattgata aggttcaatt aggaaggttg atacattgat aataaaattg aattgggatc    17880
tcactgatat atagaagatt caaagtggta aaataattcc caatagctga taagatccag    17940
agacacgcaa ttgtctgaaa ttcaatgaca tgatgttaac caacaattaa ttaagaaaat    18000
attctgacaa gtaatgtgag agtaattgaa attggtttct caataccaca agaagagtg     18060 tgaggtcttt cccagttgaa atgtcgtaaa atctccttaa gaacgagttg agcttttgaa    18120
acaagaatct aaaggtgggt tcggggattt gaaaatcata gatttgtggc aggttcctgc    18180
aaagaagctt attaatttat ttgctccaca aaataaagaa agattataaa ttaatgtata    18240
cagagaataa gattacagta ccatgtgata agtccagctg cattatacca tacgaatagg    18300
atgagcataa cggccatgag gatgtgacaa agtagagtaa gaaaattgta ttcgaccact    18360
tcaaagagga accaaatgat ggagaaccct gctaccattg ctgccgataa tatcttgtct    18420
ttccatagca atatatcagc aactgcaaaa tcagatcaat ctatcacaaa aaatcttttg    18480
aaagaaaggt acgttttttct gcatttggtc tttggaatat aaatgaacaa aaatgcatcc    18540
aatggtttga gagaaaaccc tcaaacaac  actttggtta aaagtaggaa aactttctac    18600
caatcaatgt aaaccctcaa aagtcaaaac aaccccttaaa agtgtaaaag tacaggaata   18660
aaaataaaaa gtaaaagtac aataaatgtt ttttttttct aacaaaaaat tatcacttta    18720
aatacttaaa atgaatccaa aagaaggatg ttaacatttt ccttaaaatt ttcagatcct    18780
ctatattaga atttagaaac ataaattaag acgtaagaag aaaaaagtgg tgaagtgttg    18840
ctaaactatc ttacgctttc ctccgccaag gactgcatgt agtggtcttt gacggtctaa    18900
caatcctggc ctctgtgcag tttcacggga acggattggc atggttacca atttgaatga    18960
ttgaaattat cttcgtactt tgtgttaatt tgttggttct cctgaaccaa gttctagcac    19020
tgttatgatt catgcgtcat ggtgccaact atatgtaatg ttcgaaagga tatttggggt    19080
tctaagcttt gtaaccaaga aatttaatta actactcatt ccatggagga ggaaaggtat    19140
ggctttggca tggttttcaa gttttacttc ctcgtgccca cacatgattt aagatacatt    19200
attagcgtct cacatttacc cttatctatg tgtctaatgc tatgttgttg ttttttcttt    19260
tttagagact tttcgtggga atcttatcga cacctgagaa ggacggagac ttgtcatgtt    19320
tgtgctcgac gcaaatattt gacatatgat atacaaaata ttacaattat gatttcaaat    19380
tctatatttc tttcaatata gctgttatgt atcacgctgc aatttagat cgataatagt     19440 aataacaatg tcgtcctgtg tgttttttcac aatcattcaa ctcataaaac tagtgggaag   19500
aattcataga gagtaggata tgctcaaacg gcttcatgat gtgctagtat ttaataaagg    19560
accaattata taataagata aataatgtaa tagagaaaat aaagaaaaaa taagttataa    19620
aagattttat gaatttatta tatatataat agtataatat gaatcatcag ttaattttcg    19680
tgatggacca tgtatagtca tgaagtgcaa taccggtatc agtttaatgt ggagactgaa    19740
gagttattaa tttggacgtg ctttaaaact ttgttaattt taatatcttt gaactcaacc    19800
cacattccat gacattttgt ttttgacaaa cgacccatga cataagattg atgctataag    19860
cgtgctgcta ttttcacccc ctttttttc tttcaaaaaa ccaatgaaaa gttcaaatta     19920 ccctctctc  aattctcatc tccctacaac ccctacctcc tttctcttcc tctcccctcc    19980
tcactttctg aattgtgatt ccgcaaacac ccattccatc ccttcttcca ggtccatcgg    20040
ccattgtttc cgccaaagct tcacatcaga gtcggagaag ttcttgctat ctttttattgc   20100 ttatatttaa ttaattaaat tatttttttat aataagttaa acgaacaatt aagtctaagg   20160
tttaattaaa tcaaaattaa aaaataaata aataaaacgt tgacaaaatt aaatattgaa    20220
```

```
cccaaataaa gatttttttt aaataaagag accaaatatt tttatttaaa aatgatgaga   20280
ctaaaattgc atgttagaaa aaatagagat taaaattgta tttaaagtta tgttgaacaa   20340
gacatttgat tattcagtaa ttaaattttt ttaatagttt cttgctagtg tctaatgttt   20400
attgaatcgt tatttgaatt agtattttt  aaaacattaa attttaactt tttgtatttt   20460
tttctacttt tattcttaat atatttattc attttttctt atcatatttt ttaaataaat   20520
aataatttta ttattttcta acatttttaca ctttacaaat actttaataa ctaattttac  20580
gaaatacttc taatttaata aactaacttc gaataatttt ctcaaatata acctaagtca   20640
agaaaaatta tccataaaat caagcggttt tgattttttca cttttttact tttgtaaaca   20700
taatcataaa gaaaactcaa atgttgacca tctatcatgt tgcacatttc gcatcgccga   20760
aagtcattcg gccttcagct tgagtttgaa aagctccagt ctccaacact taaaaatcct   20820
aaattcttta tgagaaccaa attactcgag atcattagtt aattatgaaa atattatata   20880
ttacataaat ttatatttac atatacaaca tttatcttca tatatgacaa taaaaataaa   20940
caaacgtttt tacagatttg acattaatta atcattgtat atatcaattt ggctatttga   21000
gatgttatgt agagcgggga tgagatttga actccttttc gtggcttacc tgtgatgaga   21060
aggcacgcta tcacagtaat tgttcagtgg cttatatcat gtccttcgca ttctgtggta   21120
ttaggtgcca cctaatttct tagtaattta tttgatgttc attgatttag cttaatattt   21180
cttataaaac aattatagtc ctcgacagtc aacatgataa ccaatatgca cttatattta   21240
atctattaat aaaactttaa ttgctcgtaa aaaggttatg aattatgata ctgtgtataa   21300
aaagaacctc gaggcttctt tttcttcttc ttttttcaaa taataatatt tctataaatt   21360
aggctctcta gtctcttgtc tgacaatgcc taaccaaact ctcgcaaact tatgggtgat   21420
aaaaaatgtc tttgatctac caagagctaa acataaatcc tctagtaaaa aatgtaaaca   21480
acccgtcaaa aaatggaggg taaagtaaat accaatactt gttaatatag ccacgcgaga   21540
attatttgtt tatgatttgt gagcttctac agagcgggaa agacattgaa gttacatttt   21600
tctaacgtaa cactgttaac attatcaagc tcgtataata atatgttcat tttaatacta   21660 gtgcttttt  atattgatgc aacttataaa tgattaggca gacacgtttg tttcataatg   21720
atggtggcaa acctatacgg ctataacccc ctagcatggc ctgagtcaaa taactgaaat   21780
ctattagcaa tgaatacaca ataataaagc aaggggggtc ctccgcaaat tcatgatgat   21840
agcactaata atccccatcc acataacata acacttgggc attgatgaaa ttggttttat   21900
agtagtcagc agccttgtcc taaggtcagg taatgttttt gttattgtt  tacagatgcc   21960 attatagcga agagagccac gcccgtatgc atccctgtgt gtcttaatct taattaagag   22020
tctcacgtat cacctctcaa ttaaattttc tccttcttag tctctctttg aaaatgaaga   22080
cctcatatgc aacattgtgc ccttctaggt cagaatgagt tgtgcatggc ggcagtgacg   22140
tgtaacgcgt agcagctgag tgcatgtgcc agcgccatca cgtcctcaac ccctccttca   22200
gctgtttgat gtagcaaact gaaggaacag aggccccaac ctcaagaagc ttgttaactc   22260
tcctaatgct aggaaggtag ctaatgcatg tggttcccca ttccccactt gctagaaaca   22320
attgagtatt tcacaagtct ctgcttggtg tggtcgtgct acaacactgt gtgccccttg   22380
tcagttgttg gagaatttga tcttgtacca cctctgtctg catctattaa tgaatatgta   22440
gtttgctgat tatgagcgct cagcttttac ttggtccatc gtacaaaact acaaataatt   22500
tctctgtcac gactctttct ctttctgtga gattaaatta taattatatc tttttacata   22560
```

```
accagttatg acttatgaga caatcatttc atttcctgct cgagtaataa gtagtattac   22620
agtaaagcta ttcgtacttc aattgaatat ctagaggaga aatgttaact gcattcctgc   22680 ttagttttg  tgttaaatct aacagttttg gactttcctc caattataaa tcattgttaa   22740
tatatttttt atgataatta tactaaaaat ctaacagtta aaaattgtca atgatagcct   22800
tgttttttgt ctctatataa aagtactcag atgctgaaca atgtaagcac aagaaaggtg   22860
tgtaaataac tagtgttttg tctttgaatt agtggccgat aaattgggaa aatgaataag   22920
taattactaa ttagtggtaa atatatagtt caacaaaaga aaaggatgag aagaacaaac   22980
ttgggtcaat tactttacat tgaggtattt gcttaatgat atccgatcgt ctttctcttc   23040
ttacgccgcc acattgcctt tgtatctct  tttaattata acggataaga gttaaaataa   23100
cagtgataat actgataaca ataactttta aacattctga tgttttaata gaggaggtgc   23160
ttaaaattga agattcctct ttgctgaact aactggtaca cattttttcat ctttatcttt   23220 ctagacttat tgtttgaagg gaaagaaaa  gaatattttt ttctataaaa agaaaagaat   23280
atagtaagag tgaatggaat gaaacttaaa gaaatatttt attttttatt ttttttccctt  23340 tttataaaat aagagaaatt atatagttag tggaaaacta aacgatgaac caaggttatg   23400
tttgtatttt taaaaataaa atattattta aatttatttt gtgataatta gataaaatag   23460
aagtcataat attattttag aattttaaaa aaataatttt aaaaggaaag attaaaccat   23520
agaagttttt cttcttcttc aaaacttatc ctaagttatc ctaaaatgtt catgaaatag   23580
ttttcctaca aaacccaaca gcaatatcta cccagaccac agacttgcct ttccccagat   23640
atccagccga agacattgcc tgtctccttc acttacctcc cttctttcac tctcaaccgt   23700
cagaaaacat attgcattta aataagccaa catatcacgc acataataat gataatacag   23760
taataacaat gcaatgccaa aatatctaga tatttaaaat ttaggctccg acataataat   23820
tgataaaagc caattaatac caaattcaaa tatcaagata gagtaacctt acttgtataa   23880 caaattttg  caacaaagtt tctgctcatt cattttctat ctccaacact cgttatctta   23940
tcacacatta agattactca tcaagatgat aaaagagaa  aaaaatatat catcaccaca   24000
aaacacgaaa gtgagagcct agttaatcgg cccttcactt tgaaaactc  gagtaaaaag   24060 gctttgtaag aaatttacaa gtttagtaag agcatctcca attaaattta agaactagtt   24120
caatacttta tgttatgatc accgttggag gaagctaaca tgatttccaa ctgtaagaac   24180
tggttcttat ataaacaatt agttcttatg attaaaatag gatattttat gagatagatg   24240
ataataagtg tgacccattt taagttcata gttgattgca tcattagaat agaaaattac   24300
tatagttctt aaacttcatt ggagatgctc aagctaattt ctactacaac agcacatgca   24360
agtgagacac aaaaagcatg tagctggagg atgccaaaac tttaaaacta gaagattgga   24420
atatattaat taaaccacca acataatact accatgacca tctatcaata tatttcaggc   24480
attctcctat tacagcataa atactatata ttcatccatt atccaaaagc aataagagga   24540
ccaccaaaat tgagtttaaa accaagaaat aaaccattca ggccttatca gagtcaggac   24600
cttggtggtg gtgttgcgtg gccaatccaa gtccttcatt gtggtgcttc tcccagaaac   24660
cagtgtcagc cttggagtgt gcccaatagt acaaaatggc ggtcaacatg gacaacaagg   24720
tcaaggcagc tccagcagca aacacaccct tgcgtagggt agcacaagac aaatcgtgat   24780
tcacaaaata ccctctgtac tttgtgtggt atgcattcct tgcagaccct gctaacagac   24840
acgcctctgc cgccaaaaaa ctaatcctga tttcacagta gtaattattg aaacaacaaa   24900
ttaataaaat atttccaatt tttcaattca atttcgtctt ctgacagcaa aacgcacaat   24960
```

```
catttcataa ctggtgtagc tgaagtgaaa gtaaaagtct atctagtaat ctatgactct    25020
aaattatgtt cagttttttg ttactaaaat aattacaaga taaattcgta gggatttgat    25080
tatttaaagg tgaacttagc agtgcgtgtg attaattgag tgataccatg agaggatgaa    25140
ggagatgacg gcggaggtgg cggagcagcc agagacgagg cctttgccgc agcaaaggca    25200
tcgcgtgacg ccgttaagga cggtgtggct gaggaggagg agggcgacgg cggagaggcc    25260
gtagacggtg gaggcgtcgg tggtgtaatg gcagaaggtt tggtcgtcgt actcgtcggg    25320
gaccactttg gcctgaaaag gaatcaaatt tgagagctca attgcggaaa ccaaagcgag    25380
aggggggtag ggttacctcg ctacgacgtc gttcggcgcc aacggcgaag acgaaggcta    25440
tgagatgcag agcgatgatg aggactaaaa tggttacaga aactgccatg atttctctct    25500
ttctctcact ccactcactg cctttttttgt gcttatgttg ttatgtcttt agcatcttca    25560
cactctcttt agctccggct tttcctcagc ctaattcttc cttttctttt tattcctaca    25620
tttcaacttc ttttttcctaa attctcattg cattttcctt ttttattttt ttaactcttt    25680
tatataatgt atgaaacaaa aatactaatt attttcgtca actgttcatc atgttcgacc    25740
atatcccaaa actcaaaaaa cattttata aatacataca aatttattta ccaataaaat    25800
tttcacatca gaatttaagt ttatgttttt gtgagatatg agtttatttt ttatttatta    25860
gacaaacctt tattgattaa atattattct tataattttt ttgtataatt gtcttaaaat    25920
tgtaagtaac ataaatagta ttgttctaat tattaatgaa aaaaatgtgt ggaccattgt    25980
ttttattctt tatttgtcgt tcaatgcatg tttggatttt ggttaaatta ttcataatat    26040
cgttaaaata ctaattaatg ttattttgga taaatgtttg cttattttat attctgtttg    26100
gtttaacgtt tctctataga taacacatgt caatgagtca atcttaaata gctttgtaac    26160
tgtattggtt aggataagta tctgcctatc cctatcccat aaatccataa ctgataagtt    26220
agctacttac tcccacccat ccatacacac tatcattata aatacacaga catttctatg    26280
ctgtatgtat agaaatcttc tcattctatt attaactcag taacttgaga aatctggtaa    26340
gaacggtaat acttttgctt ttcttgctca tttggatttg actttaccaa tttcatacc    26400 tttttttaagc aaatccaaac atgcatgttg aggaattgtt tgagtttaaa attaactttg    26460
gactaaaaca attttaggta gattttatgt tagtttaatt ttttttaacca agtttaaatc    26520 cttttaatta agatcaattt cgtataatcg attcaataat tttatgaaca attacgcaga    26580
caattctgtt taataaatgt gtaaagtgaa caataaatat ttaagtgatt aaaaaaagta    26640
gtagcttttc ttttttgttt tgtttaggct actttggcgc gaagttgagt ttgggattgg    26700
catttgtgga cgctagtgta aaagttcgtt ttgctttgag ttaattgttt gaaaagaaat    26760
aatgagatat tccctaaaaa atgatgggtt tggatacact gtgtggaagt acagggaaga    26820
ttggtgagtt tgggcactat actgccgtag actgaaatca atcacgtagc tgtgacccaa    26880
acgatggtcg tgggacccag ctagataatt attattcaag tgatttaggg tgggacccat    26940
ttactgccat cgataactgt gagtcaaagc gaaaatagct ggaacacggt tgtctggtca    27000
ctggattgat ggtaaggttg ccctgttttt taatcacgaa aatgacatat aaataacaaa    27060
attaataagc acccaaatat attaggctcc gaaactagta tctttaataa ataaaaaata    27120
aattaatttc tgtgtattat acagtatata attaattaaa gtattataca ttacacactt    27180
gacttcatta caaaagcttg tcgtggacac tgcaaagttt tcacagtgta ttaaacttac    27240
aattagcaaa tgcaggaaga aacgccttgc aaatagtagc aatctcttgc ctgtggccac    27300
```

```
atcacacgcc attgtcgcct actgtctttg ttctctatgc actgtaagtt gtaacaagta  27360
tgattgtcgg tgcggatatt gtactagaaa tctaattaat gactcacttt tatatcctcg  27420
ttaacaaatc taataataaa ttaagatata aaaaatgatg agtgagttta tgattatgtt  27480
gagcaaaagc tgaaaaccta cctcaaagtt aaaaattaaa aagttaattt attaaattat  27540
aatatttgat aaaattaatt atttaaatag ctaaaaaaat aaattaacat aaaaataata  27600
aaattatcat ttatttaaaa atttaattag aaaatttgat aactataagc taaacaatta  27660
gcctttaaaa atatattatt ttagttttgt tcaaaaaaat taattaaaaa attagtcagt  27720
tggaaaatta gtttattaaa ttataaataa tttattaaat tataagtgtt tgataaaaat  27780
agttattgaa atagttaaaa atataaaatg acatatttaa aaaataataa taaattgaat  27840
aaacatttca aggataaaaa gaaaataaaa tttaaaattt aaaaactaaa agttatcatt  27900
gtaaaaaaat tgtactttgt ttaaaaaatg ttaaaagtta gtaagaaaga ttatttactg  27960
aataatcaaa atagtttttt gggttagtta aaaactaatt aaaatagttt gtaaaagata  28020
gtcaatattt ctcataattg agagagaaaa aatacaacca tttatttcat atctaaaaga  28080
aagaaagtat tacattaaga gaaataatat ttgtacaata aataatataa catattttca  28140
aactaaaaga aataaaatg agatgtaata ataatttga cggagcgacg gaggaaaaaa  28200
ctgttgttgt ataaataatt attgtacgaa tagcacaact ctcatttaa tacttaagct  28260 catggtgaaa cttttaaaga atacaaataa aaaataaatt ctatttatta atagccatag  28320
atgaaaaaaa ttaacaaata gttctaaaag agaaatattt tcagagcatg gaaacataat  28380
taagcaattt tatacttttt agtatactaa attataaatg ctagtaaaaa taaattaagt  28440
taagcaaaaa ttaatttatg tattttttca tactttaatc ttctaatata aaaaagaaa  28500 ttatttctat gtttacctaa attgaagaaa aatatttatt tcattttttt gtattgaaca  28560
taaaatattt tttaaataaa atactttttt acataaattg aagaaaactg ttattattat  28620 aatttttag tacatataat tttaaaaaat attaacaaaa agtgactaat ttcagaaaat  28680
atttgctatt ctatttgaga tgtggtgcgc cagaatccat gatcgatcta gtcatttgca  28740
gcattgggat gtgagttcct aacatgatga gcagctggtg tagtgtttct ttttgatgga  28800
taaccatgga gtttgtagta gacttttgca gtatgtatac cctcttgat aggttatgtg  28860 ggcctgttgg aggaagaata gttattggaa cctgtgtgtg ttataacttc tttatggtaa  28920
tgtgatttga ctttgtgagc agcatgactc atcccaggtg agatagttct caaaatcagt  28980
gatgaggtca tgtatttctt caaagctgat tggattatc tgataggtgt gataattgca  29040
tgcaggatcg atatcaatgg tcctgagcat gggtggggga ttcctcgtgc ataggtgttg  29100
ttatttcttt tatttcaagt aaggctctat ctaaacatcg tcacaccttg tggcttttgc  29160
catgtttagt gttacttata ataatatttt cctttgctga taaaaaaaat aataaaaatc  29220
actgtgattt aaggctcggc tggttttggt gtcatcaaca agtcaataa ggtaatagcc  29280 aacaagagag tttaatttag accctccgag cagtataact aaatccattg agcttaattg  29340
aacttgagtg tgattactga ttgagtattt atggtaggga tattggtggt ttcatcagat  29400
gaggaagtca tggtggaaga ggtatgaatc aaatgctgtt aagccaaggc aattgacaca  29460
tatggagtaa attatcatgg gagttctcat ttttatttct ttgttattat tatagctaga  29520
gtaaatttga taagagataa gatgtatcct aatctagact aaagctgcaa gcctgcaaca  29580
attagataag atctacgttt aaattacaag ataagatatt aatagataag atcttcattt  29640
ttagattacg gaatcatgtt tatcccttat ctatttagtt agccataatt atgatgtgtt  29700
```

```
cagttaggat tctatatcca tttagttgca gtagcttctt ctcttgttat ataataaata   29760
tgtgatgagt tctttgtacc tgcatggagc cgctcgatat ggatatggat cctgacttca   29820
ggtatgctgc aagattaatt aatattcatt tatggttttc ttccattttc ttatttcctt   29880
gagccaatta cctttattgc ttgcataatg tggtgtttta ctcggttgga tgctttgttg   29940
tttggttctt tgacaggcaa ttagggaagg atagtgaccg tgatttcatg gactcaacta   30000
gtgattacgg tacatgaggg aacacaggaa tcttccttat ctagtgatga tggggaatct   30060
gtcaattctc agggttactt ttttagtat cttgaactgg agaccctctc agaagttgtg    30120
atttacaagc atcaagttgg atatctgtag cctgctttga gtctttgaca ttcagtttt    30180 acagatgaac aagggaatga cttgttcttc tttttgcttg tatgcatcca atttgcagga   30240
taccaaccga tccaacaatg aaagatcttg gattcttgat gccttctttc tgacatatca   30300
ttcccattat gaacccgtgg gaggtaggag gattttgct tcatttgtgc ccgtagcgga    30360 tttggttta taacaaagtt caagaaaaga tagtagaaca gtgtattaca ttaaacatgt    30420
tttatttgaa gaataaattt cctatttgag attgttgtgt taaaatgtta gagcattaaa   30480
tcattaacta gtttgtcata cgttgctata tgtaaaacaa caactaagca ttttcccact   30540
ggccctaatt ttctgtcttg tgtattatgg cttatgtctt ggcacctgtt agttgtgatc   30600
tttcttccat agttttgtta tttcttacca ctgtgcatta ttttattgct ttcattgatt   30660
ttagcaaatt tattagccca tttttgtaag atatgatctt cttgtgtctt gtttaaattt   30720
gtgaaatgtc attttggatt agttggggtt ctttattatt tctactacaa aaacttcttt   30780
ttttatcatg ggaacatgtt tctatttaag catacattgc caattattgg ttcatagtaa   30840
tgaaattatt gtgagatgct gcatctgata accatagtct gttttccact ttgcatcagc   30900
tatgcatttt ttctttcttt caagttcaca agaaagagt atcggccacg tgccatcac    30960 atcctactga catggacagt gtccataaaa tgtcttgctt catacaagtt caaaggatct   31020
ctggattcat aatgattggt ggatatgaat gtcaattagc tagctctctt ctgtaggcaa   31080
ctggttaagg gttcctttgc tgacaactga ttaagactgc ttcaggtcag ccgttgatga   31140
tgttaaggtg accgtagcta taaaatactt acttctgctg tttaagaact gaaccttagt   31200
atttgccagt ccctccttg gtccatttct tagatgtcac acttgctgga atcagagtaa    31260
atcacaaatt caacagaagg aaaaagggaa aaaaatggt aagctctctg tcctttgcaa    31320
ttccttgcat tgtttcctgc cgtaataagt ggaagaatca taaaagtaat ggtaaagcag   31380
cgaagctcgg cagagttgag gctatgtcag catgtgttca tggtggatac tggatataca   31440
gattaacgag ccagcttcac aaggttggtt gatacatgtt atgaggtttt tgtttgcta    31500 acatcaatga gccctgcatg gattgcttct tgttgatttc caactatatt aatgttggta   31560
tggttttgtt aaagagaaca acaggctaca ttttttctg tcctggttgg gaaattttac    31620
tgtataggag ctaggtggac tcacgtttct tagctgcatt acctgtagaa ctcttctgtt   31680
gatttactat accaatgaag ggttcctttt cttcgataa tggtaaagtt catgttgata    31740
gaactaatta aaaagttcat ctgtatttga gaatgatatt ttataagtga gttcagaaga   31800
accaagttca tttgtttaac ctaaactgca agccaataca gctaaaagta caatattcct   31860
atatatggtt atccacggtc ctacaaaaac ttgataaggt ctagttatta agttactaat   31920
agaagttagt aatactgatt ctaatttata taaagttcag tatttatagc atatgcctat   31980
ggtactttgc ccattcgttg gggatggatt tggccatttt ggttcaatat ttatactaga   32040
```

```
gtgaaagggt ttttatggta ttgtaattga aatagttgtg aattaaaggt atttcaattc    32100
tcaagtctaa cattaatctt tttaatgtgt aaagattact ccatgcctct tctaacaaaa    32160
tatattttag ataaatgatt aaaaatcaag ttttgattgc tgtatttaaa gaactcaaat    32220
atctgttaga ttttttttgaa atattttagg aagtctcatt gattgcagac acggccaaat    32280
ggcaaatatt aaaaaatcga atgcatcact actttatgaa cttgtgctag atgaatattt    32340
gtcaatcgat aatgtattgg cttgtaggat tgcggacaac cttatctagg aatatcacac    32400
tttaatcttt ttttggcttg tagtttgggt aaaattaacg ccagtggttt tcaaagtttt    32460
actttcgttg ctgatatagt agagtcttca gcatacatgt caactttcct ataaaaaaat    32520
tacgaataaa aaaaccttga catttccccc tccgaacagt actagtttgt ttgcttaggt    32580
ttgagatgat ttcaaacagt tatctgtttg ttgaaaggaa aaaatatgcg ccgagtagaa    32640
tttgttaaga gtaactttaa ccttttcgta cagtaaaatt aaatgtgaat attattatta    32700
tttaacagca agtcaaaact gattcttcta aactcaattt taaatatca ttttgaaaac    32760 agaaaaactt tttaactggt tcagtcgaca agaatttcgc caatgactaa aagcaaatga    32820
acccttcgtt ggtatctaaa atcaagaaaa agttctatag gtaatgcagc aaagaaaaac    32880
aagtataaga attcaaatag agttgggggc aattctagca tgaatacatc taacaccata    32940
tccagtaaaa tttctccaat aaattaaagc taaagtccaa ttatagaaca tcaccaggac    33000
agaaaaaatg tagcctgttc tcttttaaca taaccacaac aacagataag caactgatgg    33060
aggactcatt gatgttagca acaaacaaa tcagctagca cttgagaagc tgcttgttaa    33120
tctgtacatc caccatgaac acatttaagc ctcaacactg cctcttgtcc aaagcttcac    33180
tgctttatta ccattattgc ttttctgatt cttctcactta ttacggaagg aaacgataca    33240
gaaaattacc aaggacagtg ctaaacatct tttctccatt tttcatcttc cttctgtcaa    33300
ttatgttatt aactccaact tcatcaagta tggccatcta agaaatgaac caagaggcac    33360
tggcaaatgc taatgttcta ttcttaaatg gccaaagtat aatattacag tcaccttaac    33420
atcatcaacg gctgaaaaac tgaaaatctg ggtgactgac ttgatgcagt cttaaccagt    33480
catcagcacc ctgcaaaaga daccgctggc attcgtgtcc accattagga gtccacagag    33540
atcctttgaa cttatatgaa gcaagaccaa aaacaggtaa agacatttta tggacattgt    33600
ccatctcagt aggatgtggc atgggagcct ggactctttg tgaacctgaa aaaataatg    33660 catgtctcaa taaatcaact ggtgcaaaat aggtaatgga tcatggttat cacaagtggc    33720
atctcacaat ttcattacta tgcagtatgc gcctataatt ggcaatatgc acttcaaaaa    33780
gaaacatgtt gccatgatta aaaaaaaaca caatatttgt agttgtagta gaatgatgaa    33840
gaaccccaac taatcataca tatcaagtaa gaagaaaaca atggaagaaa atcacaatt    33900 agcaggtgcc aagacattag ccatattcat ataatcgtaa accaaggaag attgtgaaac    33960
ccaaatatgc atcttatcca ttacatacat gtatcatagt ctaaggaaag gttctaagat    34020 agcatttat cttagaacca cttattatgt tacggatgga tgcatataca cagctctatt    34080
ccatattaat ggtacatata tatgtaacat acacaagata gaaatttatg gtgtcatata    34140
ctcatacatt gcatgtagcc aatccctaca cttcctagtg gaaagggct tagttgttgt    34200 acatatggta acaaaagatt gctgatttaa taccaacatc ccaagtccta acacaacaac    34260
cacaaaaata tgaaatttat tcatgtaaga aaacttactt aatgtaatac agtgttttct    34320
tatctttccc aaacttcgtt atatagcaaa acccactaaa tcgtaaatga aaaatccatc    34380
ttacctccca tgggcatata aagagaatgg tatgtcagaa aacaagcatc gagatctttt    34440
```

```
aatgttggac cagttggtat cctgtaaatt ggatacctac aagcaaaaca taagaacaga   34500
tcagtcccct gtgtatctgt aagctgaata tgaaagcaca taagtaaaga agaataccag   34560
gctacagata tccaacttga tggtagtata tcacaacttc taagggtcac cagttcaggg   34620
aattgaaaag caagatccat tatctatcaa ccacataaaa gaaatataaa tcaaacagcc   34680
caacaaagaa ggaacaggaa taacaaatga ccaaaatccc gtaggataga gtaagttagc   34740
acaccttatc agccaaaggc tcacggctgt aaggagggtc ccgttcaaga tactcaaaaa   34800
tcaagtaacc ctgagaattg acagattctc catcatcact agaaaaccca tctggtggaa   34860
gggaatggtg gtctctcaaa gataatccgc ccatccattg aggcacctct tctaacagat   34920
ggggaagatt cctcaatccc cttccatgta caggttcact atcactgcta ccatcactac   34980
ttgagtccct aaaatcactg tcactatcct cccccagttg cctatcaaag atccaaacaa   35040
caacattgtc atacaagtag ctaactctta gcttaaggca ttcaaccata gaagcagtaa   35100
aggtcatcat tgtattgagg aaatcaaaat ggcagaaaac caaacatgaa caataatttc   35160
aatcctgcaa catacttaaa atccataaac acccgattaa aaatatgcaa agtatccact   35220
caaacccgat tgtttggctt gtatttggat tttgcacctt ttcaaacaat cactaaaatg   35280
aatcatctgt gcgggtccaa agaaagctat ataccttgac tttacagttg gcttcacatt   35340
ctgggaataa atttggatcc cagacagata cggaacatag tactgaacaa cactatcctt   35400
gtcattcagt acaagtggca ctcctgcgcc ataagcactc cattcccgaa aggattccca   35460
caaatccccg agaacgaagt aaggctgaaa ctccgcccca cacgccctga gtcctcttgt   35520
cgtcctctgc aagatccaag aaaactttca tgcttaacag ttccacacat acacaatcat   35580
aagaaaaatg agaaattcac aaaaaaataa ttatttttttt cttttctgc acaaaaacat   35640 tgcttcattt gtttctttta attcacacca aaaacatcct ctccattcct tccatggtcc   35700
cttctataat taaacacggc cataaatgtt aaaccttctt cccattgaat gctttggtca   35760
caactcacaa agacgtgaac tttaaatcga attccaataa acccaatttg aataaatgaa   35820
acacgatttc accaacaacc cagtttaata aaaaaaaaaa aaactttctt tttcaaaaca   35880
cttgttccag tgactcaaaa gcaaacctta ggcagacact gagcaggcac ggagggtgtg   35940
atcgcctgca agaaccgctc cagattactc aaccggttcg ccaccggttc acacgaagga   36000
accgcgccac tcttctttgc ctcgtccgac ccgacccggt tctccggtat ccggttaccc   36060
gaatccaccg atttgtctct aacggagcga gacgcggcaa cgtcgctttg ggccctacgc   36120
agcttgtcat tctccatagt tagaagcgac cggcgagcct ttgccggaga atagaaccga   36180
tcctcgccgc gagcgcgccc gaagttcaac ccagtaccca acattcctat gcccaataaa   36240
aagagaagaa aaaaaaaaag gacccaggaa taaaagcgg aactttaatg gataaaacct   36300
cgagtgtgtg tggtcaacgg tgtttgggat agaaaaaaaa tggttgggaa ttggatggga   36360
gcgatgagga tctgtgtggg gcgattctag ggtttggggg aaaggggttg ttgttgttgt   36420
tgtgaggaag aagggtttga gtagagagga gttgtttctg tgaatcggag agaatgaaag   36480
aaaaaataga aagggatggg tctttgagtt aaatagaaca acgttacgat ttctatattc   36540
ctgcattttc aatactgttt ttttttattt ctcttggtgt cacatgatgc tattattaat   36600
taattatatc tttttattta tttatttttt ctctccttga atgactgaat aaattactat   36660
tgttaattac gtgaatggca tttttttttct gaataaagaa gcgaacgtgg agggagtcag   36720
gaaatggatc tggtcgttgg atgaggtgga gtggaagggt aaggtagtca tttcaatcga   36780
```

```
gggctaagtg gaacgcatgg cgagaggcga aaaacaattg aaaacgaaaa aataattaat    36840
gaatgaatct gactatgacc gaccatagac taaaactctt tcttttttctt tgatttattt    36900
attgttgcta ttttttcattt tttttactgc aatatttctt ttttcttttt tgataaaatt    36960
tcttttcttt tattgaaaaa taggtatcac gcattttata aaatatttca atttgatgca    37020
cacttttatc atctgttcag atgagaaaaa aataccggaa aaataacaaa taagacaca     37080
tacatgtaaa caaattatac ttgttaaaag acgttgtttc atgaattaac atatttacat    37140
aagttatttt tttacggcaa ctattcacat aaaaaaatag ttacataagt tatgatttat    37200
aaaataaaat aaaatgccat tgtaaaattt aattttataa agatagtatt taattttcat    37260
aatagtaatt gatgaataaa aaatattaaa attaaatatt tttatttatt taaacttttt    37320
ttttttaaag ttactttaat atttatggac gaaatggaat aaaatcaaaa aatacttaac    37380
ctaaaacttt tttattttct ttatatggag tggaaatcat taaatgttt tattgtatta     37440
ttttattcaa tgactgtcat ttaattttat gtgtgacaaa ttatgtttaa attttaattt    37500
tttaataatt gtattaaatg tctttattat attatttat tcaacatcta tcagttgtag     37560
aatcaaagga ataaattgaa aagatttata ccaatgagtt atgaacaatc acaaaagtga    37620
atttggtgtt atatttaaac ccaaaacttt aatatttgag tttatagttt ttttctcac     37680
ttatatggag tttaactttt tcatttttat caaatgtgag acttcatctc atatttacac    37740
tcaaataatt tttttcctca agtctgactc tctttcacat aacagtcttc tcctttagca    37800
aaagtcattt ttaatcaata agtatccaat agtgatcctt aaagcttaat cgttgagtgt    37860
cccgactagt ctaactatta ccactaacat gttgttagta tcttgtactg ttgcaacacc    37920
tacggaactc actgtctcgc attcatgcat ggactcaccc accaataaaa cttttgaaac    37980
aatggatctt cgtgtttatg gattcaccgt cgacatctta ctcgtttgag ctggttacta    38040
agtcgaacct gactttgata tcaaatattg tacaattaag ggggataaat cgaaaagatt    38100
tatactaata agtcatgagt aactacataa gtgaacttga catcacactt taacccaaaa    38160
tcgcaaggct taggtttgtg aatttttttc tcatttatat ggtgttttat ttttccatt     38220
tgatcagata tgaaactcca tctcatactt atactctaat attatcattt aattttatct    38280
aggccaattt gtgtttaaat tttaatttat taaataattg tatttgataa ataagtgtgt    38340
tgatgcataa atatgtaatt tggtgacaat ttagttttg aaattaaaaa aaaaaatcta     38400
atttaaattt tgaatatgta aaaagaacaa caattatata ttgtcatata acttaatgat    38460
acattagtac atgaatttca ccatttaata ttaaattgat taatgaatat tatagtttaa    38520
tggcaaaaat aatctcacaa tgaacgcata ttttgtatac taaaaaacta ggtcaaaact    38580
tatattcttt caggaattag attgttaata atttacacac gaacaaaaag aatcattttt    38640
aagcaaaaat tgacatggat aaaattaaat gataactatt gaataaaata atacaataaa    38700
cgcatttaat acagttatta aaaaaaaatc aaacacaatt tggcatagat aaaattaaat    38760
gatagcacta ctagaaatgt agccttttaa tacaataaag gcatttaatg atttccactt    38820
cacataaaga aaataaaaca agttgtcggt aaatattttc attttattca ctctcgttca    38880
taaatattaa agtaacttaa aaaaataaag gaaaatagtt aatattaata aattgaagat    38940
taatttaaaa ttttagttct ttcaaattgt caatcattta tatatttagt gatcaagata    39000
ataatatgtt tttttttatta ttattgaatc aaagatggtg ggtgtctctt aaatctcaat   39060
cgacaaaatc aaagactaat tttatctgta atacatggct tgaaattaat ctaagaaaat    39120
tttatatgca taaaaaatta aacatgaatt attctcttat atataaatag aaataaactt    39180
```

```
taaaatttgt caaccttata agttaataat ctttttact ttaattgtat tggtacgaaa    39240
actaaaaaga aattctgaag tgtaaatgaa acctaaaaaa ataatttata cacattcaat    39300
gagctgccaa tataaattga tggattttt ccacaaatat catacgtaga cctaattatc    39360
tccccacttt atacggaatt aaccattttc aacacattta tttaaaaaaa aacatttca    39420 acacatctaa ctcttctcac aaaaaaaaaa atggtaaaaa acacatttaa ctctttta    39480 gtaatgatct tttctagaca aaacgatagg aatgagatga atcttcaatc ttaggggtgg    39540
gtacaactta aaaaataatc aactagtttt gaaaaaaaat cattttgatg catctctatt    39600
taattatggc ttcttatatt tttatagcat attatcaatg tgtttagatt ttttactaa    39660 tttgaataat attattattt ttatatatga aaaagatatt ttaatttggg aaaaaatata    39720
aactaattta cactgaaaag taggaggtca taattcgaga gaattaatta ttaagttacc    39780
taataaattt taataaatac atagaagttt atttgagaaa ttactacgat tattttatt    39840 tatttaatta aactataaaa tcatttaaca aaatatatag gttcggtatg atggactaac    39900
atgattttac acttagttgt aaatgttaga tttgactgat aactttagaa tttaaagatt    39960
ttggtcaact tcgatatccg ggttgcacag ttcgtgtcac tttataaatc gtactcactg    40020
tatcacactt tcctcccata tttggaatat gttaaaataa agttatctca ctaatttata    40080 attttttta gatattattc taagtactaa tatttagctt gaagtttata attctttatt    40140
tttattatta tatttattcc tattttttaa taattttatc atttatcatt tcatttaata    40200
ttaaaatatt gctttaataa aataatgcat taaaaaaatg gtggaaattg aactgcagct    40260
cgtgatcacg gtaagatgtt tatttgtgtt ggtttgttg gattttgaaa agacaaaaat    40320
aggcttttgg atgtgagggc tgaggatggt gaaagtaacc gcgggaaaat gatgatgatg    40380
gatgaaaaga tccgaaattg acgacagctg gtgatctgtg attggtggaa accaaggcac    40440
tcggattcgt tatcagcacg gtgacacgtg tgccagagag aaagtgtagt acacgtgtac    40500
ggtccttatt taaggctgta acactgttga agctgtcttt ttcttattta tcctcctaca    40560
tttttttaag aagaaaaaag taaaagaaac tcctctttaa catcatctgt aatttcggat    40620
cacgaaaata aacacgtgaa cacacgaagt ttttgttatt ttaaagtaaa aaaaaaacat    40680 tttatgctt ttttatgaca atataaaattc tctattcaca tcaatttaaa aataattttt    40740
aattatgttt aacagtttaa aactaaattt aacaaaattt aatataaatt aatatgagat    40800
cacgtatctt ttcattttta tttaaattga tgagacgctg agaaacgcag catcatggcg    40860
cgtcgtaaag cgagaataaa agagttgggg tcagagaatt tttgaatcgg gtcgctttgt    40920
tttatttgac cggccaagtt gaaataggtt cgcacgctta gagggggttta tgatttgatg    40980 tgttataat ttggtttctt cggatttatt taattaaatg tttagtttat attttttaaa    41040
aaattcattt agttaaatgg gttaaactta agtctataaa aaacttgtcg atttatttat    41100
atatttaaat attattaaaa ttaatatata tatatacact attgtattta ataatcttat    41160
atcataaata aaataaatat ttgaaataca aaaatcttta aataggttaa tagttcatat    41220
caaatctaaa aagtctttga taagttaata ggatagatta gatcttaatt ttgtataaca    41280
aatcatattt atctatgtaa aatttgtctt aatctagttt attttcaccc atatatagta    41340
ttagaggtta gcctatcttt gtgtatgtag taaataagaa aaataatgtt tttagtagtg    41400 taatttttt tttattaaat ttagttttga tctttatatt ttaaatccat aaaactaatt    41460 ttgtattat aagattttg tgtatgtgcc aagagaattt acaaaaatgt gactagtgat    41520
```

```
aatattttt   cacagttaag  agtgttttaa  aacaaaaaat  aaaataaata  taatttagaa   41580
cgactgataa  taaaaaaact  aaaaagttat  ttagaccta   catttatcct  taattgtaaa   41640
aaaaagaaaa  aaacaattga  gcttcttttc  cattttaatt  attaaaaagg  gtgtgactgt   41700
gtaaggtaat  atgaaatttg  aaaatatgat  cgtgatcttt  tatatatatt  tcgtatatat   41760
atatatatat  attaaaattt  gtgaataatt  tttttgttcg  tatccatatg  tcgatcaaat   41820
aatagctctt  gaggtttgta  agataggtat  cgtaatgtga  tactttgtaa  agttttttgtt  41880
caattataaa  ccatatatat  taattaatac  attaatttgc  aaaaatgaat  tacattgatc   41940
acctattaat  caatctcata  tatattattt  taatttatga  aaaattataa  cctaccaaaa   42000
ttaatttact  tggatataat  tataacctac  cgaaataaat  agttaaatat  attccatcaa   42060
gctgcttatt  ataacatata  cgtaaattat  gtaacaagta  atattttttaa aaaatatata   42120
attactatat  ttaattcatt  gattttttgtt tttattcatg  ataattataa  ttattatatt   42180
taattcattg  atttttatttt accatgcaag  aaaaaaaata  attacactaa  ttatcaatca   42240
atcacatata  tattgttcga  atatacaaaa  aattataacc  cactaaaatt  aagagttaaa   42300
tatactttgt  caagttgtct  gcaggagcat  atgcgtaaat  tagacaatat  gtaatatttt   42360
aaaaaaatta  taattactat  atttaattca  ttgattttttt tattcatcat  aattataatt   42420
agtatattta  attcgttgat  ttttttactg  tacaaaaaaa  aactcctttg  aaatggtata   42480
taaatgatta  taaattaatc  atttgaaatg  ctattaatca  aaacttacca  tcaaggtgc    42540
atcatttctt  cgttttttttt atcacaagtg  gctcctaaat  atgatttaat  gttagggatt   42600
actctaaaaa  aaaaaaatta  cgtcaccggt  aaatgtgata  catttacaat  tttctccaat   42660
gcaaagagat  ttttgtatca  agctatatgt  ttctttttttc attttgatta  acaaaacatg   42720
catgattat   tgacatatag  cttggtccaa  aaatctctca  ccaactaaaa  agttaggatc   42780
aaaattctta  tgaaagactt  cagtaaatga  gtgtatgcta  ataatgtttt  gtggaataac   42840
tggtttaggt  tatgtttgaa  atgattaata  ttcctttcaa  aacttaattt  aaatggatgc   42900
tttgtggtac  ggttttcctc  accatttgta  tgcacacatc  aaactttgat  agcaggtaaa   42960
tctccctttt  cctaacttgg  accgaaagat  gttgataagt  tggtttcgat  ctacgacacc   43020
aactttattc  ccatgcatga  caagttttta  attttttttat tcaaagtcaa  cttttttatt   43080
ttaaattaag  agttgcatag  tattattaaa  aaaaaactag  aacattaaat  ttacattgct   43140
tatcattttta tttttattac  aaataaaatta taaatatttc  aaaaatgtaa  attttgtctt   43200
tttattttct  tcaaaattct  actttcaaat  ttactctaaa  atgctagag   tatgtttagt   43260
ttgcatttcc  atttttctgtt tttatttttct attttcattt  taaaaagatt  aggattctga   43320
aaacatattt  ggtttgattt  cttattttct  attttttagga aataaaaaca  ctaaaaattt   43380
ataatatgtt  gacttcttgt  catttcgttt  ttagtgtttt  cagtcgaaaa  caagaatctc   43440
attttgggta  aaatgaaaat  gagatgacaa  tgaatataat  tttaagcaat  attttgaaaa   43500
tgaaaagagt  tttcagaaaa  taaaaacaga  aaatgaaaat  gcaaaccaaa  cacacccta    43560
ttgttttcat  ttttttgattg tttttagttt  ttattttttac tgaaaatgtt  ttcaaaaatt   43620
taaccaaata  catttttatc  accatttttct attttcggta  aaaatgaaaa  cagaaaacaa   43680
gctaaccaaa  cacccttaa   ttttttgtatt ggggagagag  gtgaggattg  gaagaggaat   43740
gatatcatcc  aataatttaa  ttgaaagcta  tcacataata  aatttattga  attttataaa   43800
tttataataa  ttatcttaca  aattatgtat  ttaaatctga  acagatacat  aattattcta   43860
gtttaactga  tggaatcaaa  cctcccttgt  gatgagatca  aatattatac  ttaaaacttg   43920
```

```
tgtctcatgc gtaaagtgtt actaaaagaa tttaacttaa ttgattaaat aaaatatata   43980
ttataaattc gttagtatcg tattaaaaaa aagttgaaaa acaaaatagt tcacatcgaa   44040
catgagacac aagtttgaag tgcaatcttt aatcccttca cagcggctgt atcatttcat   44100
ttccctttct tttatttagt tactctcttc agtcaagagg ctaagcgctg tttaaatgtt   44160
agtctgtttt agatcaggcc cacgatgact caagctaaat acagtaagaa tctccttaat   44220
ccttcaaagc attcattttg atccacaaat tacaattact gaacacaaaa tcccgaacag   44280
tcactaaaac agaattatcc ctaaaaaaat tatttatgtg aattattact ataaacccta   44340
atgatactca caaattgcca aatcagatct aaacaatgat caccatttct cttgtcacat   44400
gattgttaat aaagaccagg cattttttgga aattaaaaca aaaaataatg caacttcaaa   44460
agtattatgc tttcttttac tcaacactct actggacatc tactggacat aagacatgag   44520
gcacgagatc atcaaacgag aggtaataat aggtaattca taaaaaaaaa aatttcacat   44580
acacattctt aatactttt ataacactat tttctttact attttatcca gaacttctct   44640
ttctctcttg tatctttctc aattctcata atactttct tacaaatcat aaaaaaagtt   44700
gcatatacaa tttctcgtaa gatttaaatg cattttttta tattattgtt caattcaaat   44760
ttatgtaata agactttgta ttaaaagtca acatagatta ccatataaaa ttctactaat   44820
tccgatctaa gttacccatt cttattcata aatttatgac aggggggttt tgttatcaag   44880
attagcagaa caagtaggat atttctgaac ttaaaaacca tttaattttt cttgctctct   44940
aatgtccaaa taaacaagt ggtcagaagt tagcaaattt ggtcaacctt ttcaacttgc   45000
ctacacgggg ttccattcaa agataagagg cagagacaag ttgtcaattc cgtaggcggc   45060
catcccctca cctcactctc cgcatcttct tttgggtata tcatattctc tcttcttcaa   45120
tgttctctat ccacaaccct ccaaaatgaa catcttcttt atcctcagat ccctctcttc   45180
tcccctgatt ctctcctaca tcatcatctt ctatctcctt gccaaaaaca cctcctgtgg   45240
tgtggaccca aaatttcttg catgtccacc cacaacctgc gccaacaaca atcaaagtat   45300
aagttatccc ttttacatcc aaggaaaaca agaaccttt tgtgggaatc ccggttttgg   45360
catctcttgt ggcccaaatg gttttccaat ccttaatctg tctataccca atacatcatt   45420
caccaaatat ctacgaaaat cagacacttc gagtgtccaa taccgcgttt tcagtttcac   45480
gaccaaacac caccaattcc aaaggttgtc ttcctcttcc tcttactcag aatctccactc   45540 ttcctagtac ccgcgagttc gatattgctc cgaatcaaac agacattaga ttgttctacg   45600
gctgtgggtc attgccttgg ctggaagagc acaaagttgg gtgctttaac gaaacgagtt   45660
cagttctggc attgtataaa gaggataaaa atataagttt tgtgtcaaag aattgccagg   45720
gcgaggttgt ggatacgata gtggaagatg gaataatagg agggaatgaa gaagcgttga   45780
caaaagggtt tttgctgacg tggaaggccg gtaactgcag cgtgtgccac aacactggag   45840
ggaggtgcgg cttcgatttc gtcatgtaca ctttcaggtg cttctgcact gacagagttc   45900
attctgccaa atgtggtcct gatgatgatc caggttagtt ttttctaatg accaaaactt   45960
ctaataaaga caatgaccag gttattaaaa tgtatggaga catgtaacgt ttactcaaac   46020
ttcataattg caatggctgc atggttagat gctttgattg gaaattacta gtatatataa   46080
aggctgccag agaagactta attaatttaa aactatttag tttatatggt tgcaattggt   46140
gtgttttctt cgttttcagt ttaaaaaaaa gagtaaagtt taagactata caatactata   46200
acagaaaact caacagcaaa gttctgttaa cactaaacag aagtatcttc agtttgtttg   46260
```

```
gcaaaagaaa ggacggggat tggtctaatc agtctcgaat gatggttatg tgagtgaaaa    46320
aaaaaaatag gtgaggtaga ataactacca aacgaattag tcaaaccata atttccattt    46380
tagcctgtta atactatgac ttatgagatg aaggggtcgg ggaagcaaaa atcttttttct   46440 atttcagttt tttaattttt aattagaata ataatattgt gaatgaataa caatactatt    46500
ataaatttaa attgatgtta gcacaatttt aaaataagaa agtcacacct atatcattta    46560
gttgacttca aacgaatttt gaatattcca aacaactgct tgttctttt cttttttca     46620 atttcatgat tgatacatta tcaataattt aggtcgatgt tcaattccta cttttcaatc    46680
taggatggat ggctcttatg tctacgtttc aatgcatata ttttgttatg ggttatatta   46740
ctgagaactc taaagatagt aactaaaata tatttaattt acttcattaa atatttataa   46800
ttatttgaaa aaaatattaa atacttttt tatgtttatt gattgaggaa atattagatt    46860
tatacatatt agtttttatac ttttccaata atagtggaat atataaaata gttactggca  46920
tattgaaatt aatgagatat tagaaagata attaagttga agagagaaat tgatagaatt   46980
agtgaatttt aaataaggat aatttaaaca tttttttttaa ttaaaaacac tattaactga  47040
tttctacaat ttttaatat atgtaaatta ataaaaataa cttataataa aaaaatggag    47100
gaagtatttt tcaatccttc aatatgaatt ctcgttgaaa gaacacacat actaaagata   47160
gagatattct atcaccctct gagagagaaa gaaatacact attaagtagt attaagtatt   47220
agcaataatc ttttttgttt tcttatactt attttgtaaa atacatatat tttttaaaat   47280
agaagaggat ggaaaggagg aagcggggaa aagatgggta taattaataa aaataaaact   47340
gaaagttgaa aattaaatta acttagaagt gttttaatat tttagttctt aaaactaaaa   47400
atgttatttt taaaaaaaat tcaaaactac tttgaacaaa catgtaattt tttgtctta   47460 aaatatatat ttttaaaaat aaacaaataa gcttaatata ttaaaagagt ctaatttaat   47520
tggttgaaaa aaatgcatga gtgtcataga gcctggtata atttctaatt tttttattaa   47580
attgtactta tttgttaatt atcattgaca gttgacagta agcttttatt taaaaactta   47640
caagatgcct aaatataata acaagtttta aactataatt aaacagaaaa aatagttacg    47700
taactatttt tggaagtaat aaaaaaaagtt taaggcagtg aaccggactt tctattgtaa   47760
ttcgttttct ctttccgaga aaactatatt accgcaatag atattaagat gattaaacat    47820
tttaactttt gattttgcat gaaaaaatat aattgtattt gatactgacg ttaaatggga   47880
aaagagcatg taatatagtt tatttggctt gataaataac tttagtggta tatcttaaaa   47940
tcttaaatta ttttttttatt tcacaatccc gcaaaacata aaatcaaaga ttttttaaga   48000 tttttttat tttttctt attattagat tttatttctt gagatcttag ataacttaat     48060
aagtcgtgta tgcatcatac ttttaaatat tttatttaaa ttttatattt tttctcttcc   48120
cctctctcat tcttttttt attttttta ttttccttc tctctcaagt ttcacttcc      48180 cttccccttc tcttcttttt atttccttt gttgctctag catcactaca tcagtatatg    48240
cgtcatatta tatatataca tcagtgtatg cgtcacacac acacacacag atatatatat   48300
atatatatat atgttagtgc atattctgga caggacaagg agctaattta gtaaactcag   48360
caaaaaaaaa aagagagagc taatttagac taacttaaac tataattgtt agttctctga   48420 aaagatatt ttcatatttt ggactttccc tcttaccttt ctatggatta cccaaatccc    48480
aattcttatg tcaaaatttc tcacattttt ttcatgttta ctattttag caaaattcac    48540 aataatgggc tgaagcctga agttacttgg ttgggccact attaggctgg actttgttac   48600
tgccttttaa gaatttcgtt tttttccct aaaaatgttt agtcacattt tttagcaaaa    48660
```

```
tcttttcaaa atgaccttag tatgaatgac caagttcctt actaaattta aaaacagcta   48720
tccaacttcc tgtagcaaaa aaaaaaaaaa aactatccaa ctacaagttt gcaacaattc   48780
aagtaacatt ttcacaacat ctagaccaat aatgctataa aaaaattcat aaatatatat   48840
ataccbgttg aattaagtct attgacttat ataaaagatt agatatccta gtttattcca   48900
aaattgatct actagtttat taaaagactt tactaaaatc aaattttaaa tagactttta   48960
atttatgttt gagttatttc ttttttaaa gaagattaga tcttaaaaaa agtcaatatc    49020
aattaaatag attacactta atcctcatat taaaaaaata aattaaggct atcttgatct   49080 attttttaa aacgtgacta tatagtaaac gtccaaggtg gtccataaaa gaatacatgg     49140
ggttataaac atcaagtcgg tccttcataa tctaaaataa gcatcaattt aatctagatt    49200
aaattggagt ttgtttaaat attgaaagac aaaataatgc ctaaaatctt gaaggatcaa    49260
cttaattaac atctcatata atcttaaagg atcaatttaa agtatctagt gactagtatg    49320
aatgtaatat tcaataggat ttattggaag tgttctgtta ataaaatctc atgctaaaat    49380
aagcttttct gtcagctatt ggtatagaag agaagttttt tatattgaaa aaataggaag    49440
tttccacaaa gtcttccagt ctaaattaga atatagtctt tgattgaagg taacttattc    49500
aattatacaa caacaacaaa gtgccttctc ccgctaggag atagaaactt atttaattat    49560
attctatgat actcgaacca tattttataa aaacttgccg ctccctcttc ccaaccataa    49620
aggattttgc atactttta tccttgagtg ctttttataag ttttatttaa ttgaaatcta    49680
aatggttaaa ttcatagtta aatattccta ttagcaattt ttttttgtta agaagtatga    49740
tccatcaacc cgttttactt tctttttttt tgtgtgtgat tgcaacccgt tttacttagt    49800
ggcggaacag atctaacaca cattttatca aacactactc gttcacgtaa ttattctgtg    49860
aaggctatca caacaaatcg gcgatcaata ttactttaat tttcactaaa aaaaaaacat    49920
tactttaatt tttagaaagg agccctgctt cgaaattagg tctgaagttg aagaattcaa    49980
tggtactata ccttaattt ttcccacggt ctaatatgtt tggatgtagg gcatataata    50040
ttgaaagtga cgtgtttctt atggtatttt atatgctacc aatatggatg ggggagatga    50100
tacttacctt gagtgctact attgttgaga tctgaatccg ttagatgaat aaatgcttt     50160 ttgagatgtg ttaaagagtg agtatccaaa ttattctctg aaaataaata tttaaaagac    50220
tttgattctt aaaaaacaaa ctatttagtc tttcaaatta taagtataag tatgagagac    50280 ttcagttta gtctatacgg agtataaata aatgaaccat attcataatc ttgagaaatt     50340
atttgctaac ttttctgta agatttaaat taagtattta ctataaaagt atatttaagg    50400
gttccataac aacacttact cgtggtactc acttattaat tgttgatcgc tgtagaaatt    50460
gattccaact ttaatcgaac ttttatcatt atgatttatg agttcaaatc taacatggtc    50520
actttaggca gagttttgta gataatatat acatataaat acgcaatgga gtaatgccaa    50580
ttcttagtcg taaggttgaa cgggaataac ttcctttgcc tttaattatg aattcccaag    50640
ttttcccatg gaagactcaa catgaacctg ttcctctact taaactttcc cggctccatt    50700
tccctgatcc ttatttccca gtctctttc aattagagtt aagctttctt catcttgatt    50760
ttttaatagc acccttacat tgaaaggttg ctaatccaat tctacttcct tacaccgatt    50820
ctcttttggt cattttttgc ttaaatatga aacttatttt taaacaaaac ccatgattta    50880
ttgtcatcat taaagtttga gagactatat tttattaaaa agttgctaaa gaactaaaat    50940
tgggcaagta ttcgattttt ttttttaaaa gacaaaagat tcaataacat taaaactgtc    51000
```

```
caggctacaa gctgtaacca agaccaaaac aaatacatag caatatcagt cccatgcgat      51060
tggacaaaat actaaaccca taaaacaaag ctaataatga agcatgaatc agccataata      51120
catgtataac ccctgctacc aactaataaa tgttgataca gaacttccac ccttatttac      51180
tgattactaa taagtacatt aatcactcat gattgacttc catctttgtt atattatatg      51240
gtacacaacc tttgaggttt aaagtgcgta gagattaaat tatgggatcg ggtcataatt      51300
tgatatggag aatcaaagtt ctggaacctc aaatatacag tgcgtagtga taagttatga      51360
gatgggatcg taatccgatc cggagggtac aatggtgaaa ttattatata gtttgatact      51420
ttgatatcat catattttca tagcaaaaaa atatcatcac attatcattg tatttgtttt      51480
agtaaaaaac ttaaattttc tatatactat tatttagaaa aaatgtagaa atcaatctag      51540
actataatat tcatcggtca tataataata tttcctgttt tatcacactc gagaagttgt      51600
ttttaggcag acgtttagtt tcacaagttc acacagagac agagagagta ctagaaaact      51660
gagaaatgag gcccagaaat ttgaagccac tgattatgac actgaacgcg ttttctatct      51720
ggcctcgttg actggtcacg ttgaagtgaa gtgtgaacct aaccgcttaa aacgacatca      51780
ccattcgtta acgttgtcta attgccttat tatttcccac actctttcaa cgtcattcgg      51840
tactcttttt ttctgcctct ttttaagtat ttcaacctca gaggcccact gcatttccaa      51900
actcttgtgg actcgggacc cttcccctgt gatatctttc ttaaaaattc attactgtgc      51960
aaacaagtgt ttttaaatct gatatgcgtc tgatacacgg tttaacaagc ctcctagacc      52020
aagactagat tcggatgcgg aagggaagtt ttgaagcaga gtcagttcag agattataag      52080
gagtgatcaa acaagtcaag tctttgtgct tgtttcaaaa ggcgttagaa agaattggtc      52140
tcactttctc ttagggccag atatgtgtgt atttcttggt ttcccactcc ctctttcatc      52200
ttccgtagtc atcttctaat tcaactggga ggagtataaa aacaagtcag acaaacttga      52260
gcttaattta cagttcagag aatcaaatcc tagttgaatt ctgtttgctt ttagatcata      52320
gacgtactgg gtgactgagg aaggatgtgt ggagtttatg aatttgtatc attgcttttg      52380
ttttgtcacc ttatgccact tctattggcg gcggcttgtc cacctctgct ttcttgtgga      52440
gatcttggca atatcagttt cccctttact acaacagaac gccccgactg tggcttttta      52500
cccatacgga attgtgaaga tccactcaag ttcaaaatga tccaattaca gaataatgga      52560
gaatggtttc gggttgtact cgtagctcag cttcggaaca gttctatcat aacttttcaa      52620
attagagaca aacatctcta tgaccttctg cagaacgaaa gttgtgaagc tttcagatac      52680 aatttatacta ttcctcccctt cttttcacttt gctgctttac gtatccaata ccacacaact      52740
ctgttcaggt gcaaccgcag cctccatgtc agccctccca cgggcatgct taattataca      52800
aaatgccccg actacgatct ctactacaag cacatcatca cggctgatga tgtgtctcgg      52860
agttctttgg tggcatgtac agaggtccag cttccaatta aagacgtgcc tgacgctata      52920
aacccattta cctttgtaac tgcagatatc atcattcgag tagacttaac tgatgaatgt      52980
gcagattgca actatcgcca tggagggcag tgcaaacttg acagcacaga gaaattttgt      53040
tgtgccaatg gtataaaaca acaaaaaccc tgaaaacaga agcacccacg aatgcaatgc      53100
actaatcctt gttgctttta tctgcttttc ccattttagg ttcttaaatg tttccttcac      53160
aatttgtgaa acattgtcta ctttttctgta aatgtcccaa gcccagttcc ttctcctaca      53220
tcataaacag aataaaatat tcaaaatagg tcaagaaaag tgacattgat gatgtgccta      53280
atctaagttc tcttcttgtc ttaaaatttc aaatgtacag tttactacac ttagacggca      53340
aggtctgagt tgctctgatt gattgtctaa tgtctaatat tattggtgca acagtcacaa      53400
```

```
ttagcatgcc atattttcct ctgcttaact ttatcgtcac gcttcaaatc tgtgttattt   53460
gctaaattgt ttcttctaat tgcagcagtt ataaagaaag ggttgagttt gaaggccaaa   53520
ctgggtatag gtaatgtact gtttacataa cttgatattc cttttcaaca tatgacttca   53580
aaatcactga tcctcagtgc gaaagttcat ttgtgtgttg aactcagagg gtctgctgat   53640 ttctttctt ttaattccct tatttccccc tcaaaaaaca tgagaactta tttaaaaaat   53700
ttgtataact ctatgtctct atcaatgctc attgctatct atcagaaaag tagcagcagt   53760
cacgcactct gttatttctc acggtatctt caattgatat tttctcttgg cccgtttgca   53820
caggtttagg tattggaatc ccaagcatgt tggcaattgg gttgctgttt ctctttctac   53880
aatacaaacg aaaatatggt acctcaggcg acaattgga gtcaagagat cttattctg    53940 attcctcctc aaatcctcat ggagaaagta gtagcgagta ctttggagtt ccactcttct   54000
tgtacgagca gcttaaagaa gcgacgaaca atttcgatca caccaaagaa cttggagacg   54060
gaggcttcgg tactgtctac tatggtagga tacttaatca aaccctactt gacacacaac   54120
attactctcc ttgtatggtt tggaactact acatgctcat tggtcctagt caatctccaa   54180
gtatccaggg tccggaacta ctatgtgtct gtggtcctgg tcaatctcta taacacgcat   54240
agaagagtct tatcacttct ttctcaaaat tgaaaaaact cagttaaata tcatagagat   54300
tggacagaac aatgaacatg tagagattaa ttggaatgat gaatgtgata gtcctgaact   54360
atataataat ttcttgtctt atttttgctg tataactgag atatttaaat taaaacacag   54420
ggaaactccc agatggacgt gaagttgccg tgaagcgctt atacgagcac aactggaagc   54480
gagtagaaca gttcataaac gaagttaaga tcctcacacg tttgcgtcac aaaaatcttg   54540
tgtcactcta cggctgcact tcacggcaca gccgtgaact cctacttgtg tatgaataca   54600
tttcaaacgg cactgtagcg tgtcatctcc atggtggatt agcgaagcct ggctccctac   54660
catggtctac acgaatgaaa attgccgtag agactgctag tgcattggct tatctccacg   54720
cctctgacat cattcaccgt gacgtgaaaa caaacaatat tctcctcgac aacaactttt   54780
gtgttaaggt agcagatttt ggactttcaa gagacgtccc caacgatgtc acacatgtct   54840
ccacagctcc acaagggtcc ccaggttacc ttgaccctga atattacaat tgctatcagc   54900
ttactagtaa gagtgatgtg tatagttttg gggttgtgct tattgagcta atatcatcca   54960
agcccgctgt tgatatgaac aggagcaggg atgagattaa cttgtcaaat ctagccgtaa   55020
ggaagattca agaaagtgca gttagtgagt tggttgatcc ttctcttggt tttgattcag   55080
attgtagggt tatggggatg atagtttcag tggcagggtt ggcttttcag tgtttgcaaa   55140
gggaaaagga cttgagacct tctatgtatg aagtgttaca tgaactgagg agaattgaga   55200
gtgggaagga tgagggaaag gttcgagatg agggtgatgt tgatggtgtt gcagtttcac   55260
atagttgtgc acattcacca ccaccagcct cacctgagtg ggaagaagtt ggattgttga   55320
agaatataaa gcctacttcc ccaaacactg tcactgataa atgggaaagt aaatgtacta   55380
cgcctaatat cagtggttaa tcatttagtc tattattaat tgttgataat ccgttttag   55440 tttttactat atcaactttc acctcattat tagttgagtc acagtatatt atcgtcgcat   55500
tcgcttgttt aattgtgaag ggtatgatta aattatacgg cccattgtag tcaagcaaag   55560
agttgaagtg agggtatgac atgtgaatat tagaaacacc ggtacaaaaa tacgaccaac   55620
aatttcaaac gaagttattg acatgaataa gggttttcat ttcctacttt tttaagagaa   55680
tctgacggta gagagcaagt tgagtcagag tgtaagcaaa ctggtaaatg ttaaaaatcg   55740
```

```
ttgcattttg taatcataaa tgacgttttg tggtggcaat tctttacggg caaaatgga     55800 atcattgtta actctaatca tttaacaatc acattttgt tagacaaaaa tggttcaatt     55860
gtgacatgtc tgaaatgaga gagcataaat cgacatttta aaaatgagaa actattacac    55920 aaattttct atatttataa taataaaaac atgtttaaat tggtttgtta catgaattat     55980
tggtaccttt aagcacccttt aatagatggg ccaatatcct tgtgactttg ggtacattga   56040
ttaacaccat taagcattac ttgaattgta tggacatgaa ggaaatctta ccatctttat    56100
ctgttgagct tcaaatggtt gtctgaccaa aatttccacc tttaagggca atgaaggtat    56160
tcttgttaac tcccgtcctg tccttgtggc aatatgctgt atcgtccata ggagaatttg    56220
aatggaaaac acggtgggtc atgcatcact actgggataa cgatttgtat ctacctcttt    56280 tttctccaa gtctcccacg ctcatttccc tagtcaagtt gttgttaaga gagttcatta    56340
cttgttcctc ggaaaattgg gaaattggga tggctccggt tgatttgttc tgcttcccct    56400
tgttttcttt ccttctactc atcctgcgcg ataccagagg cattctatcg tttgtgtctg    56460
ctgagattgt tcttgaagta gtattatcta atgattgtta tgagtgctat aatctccgtg    56520
gcttgacaag gataaaacgt tcaactgtac tcaaggtacc cttggcataa attttcata    56580 agttacctct tattccattt gattgctaca attccttgtt agttgttctt atagcgttag    56640
accggattag tgagtttgct gactgcta                                        56668
```

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ggaaagctta aatgaaacat                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gtgtgcccct tgtcagttgt                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gttagacgaa aaaccatatg                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ggtgcgaacc tatttcaact                                                 20

```
<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gccaaggcaa ttgacacata                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gatcgcgcag gatgagtaga                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gtggcctctg tgcagtttca                                                  20

<210> SEQ ID NO 19
<211> LENGTH: 93
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(69)
<223> OTHER INFORMATION: n is either absent or a, g, c or t

<400> SEQUENCE: 19
atttaactga aagcttaaat gaaannnnnn nnnnnnnnnn nnnnnnnnnn nnnnnnnnnn       60
nnnnnnnnnt gttggagaat ttgatcttgt acc                                   93
```